(12) United States Patent
McCauley et al.

(10) Patent No.: US 8,047,051 B2
(45) Date of Patent: Nov. 1, 2011

(54) GAS SENSOR

(75) Inventors: Kathryn M. McCauley, Durand, MI (US); Charles Scott Nelson, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 783 days.

(21) Appl. No.: 12/143,505

(22) Filed: Jun. 20, 2008

(65) Prior Publication Data

US 2009/0314056 A1    Dec. 24, 2009

(51) Int. Cl.
*G01M 15/10*    (2006.01)
*G01N 7/00*    (2006.01)

(52) U.S. Cl. ..................... 73/23.31; 73/31.05
(58) Field of Classification Search ............. 73/23.31, 73/31.05; 204/424, 426, 428, 431
See application file for complete search history.

(56) References Cited

U.S. PATENT DOCUMENTS

| | | | |
|---|---|---|---|
| 5,246,562 A * | 9/1993 | Weyl et al. | 204/424 |
| 5,711,863 A * | 1/1998 | Henkelmann et al. | 204/428 |
| 6,322,681 B1 * | 11/2001 | Weyl | 204/424 |
| 6,672,136 B2 * | 1/2004 | Kojima | 73/31.05 |
| 6,878,252 B2 | 4/2005 | Weyl et al. | |
| 7,563,118 B1 * | 7/2009 | McCauley et al. | 439/260 |
| 7,637,145 B2 * | 12/2009 | Yamauchi | 73/31.05 |
| 7,645,153 B1 * | 1/2010 | McCauley et al. | 439/260 |
| 7,775,820 B2 * | 8/2010 | McCauley et al. | 439/260 |
| 2001/0025522 A1 * | 10/2001 | Kojima | 73/31.05 |
| 2007/0072428 A1 | 3/2007 | Chilcott | |

OTHER PUBLICATIONS

Co-pending U.S. Appl. No. 12/143,395, filed Jun. 20, 2008; Kathryn McCauley, Charles Scott Nelson; Connector Retainer.
Co-pending U.S. Appl. No. 12/143,321, filed Jun. 20, 2008; Kathryn McCauley, Charles Scott Nelson; High Temperature Connector Body.
Co-pending U.S. Appl. No. 12/143,523, filed Jun. 20, 2008; Kathryn McCauley, Charles Scott Nelson; High Temperature Connector.
Co-pending U.S. Appl. No. 12/143,538, filed Jun. 20, 2008; Kathryn McCauley, Charles Scott Nelson; Radial Crimp Seal.

* cited by examiner

*Primary Examiner* — Daniel Larkin
(74) *Attorney, Agent, or Firm* — Thomas N. Twomey

(57) ABSTRACT

A gas sensor with a high temperature electrical connector is provided. The electrical connector incorporates a ceramic connector body having a pair of opposing ceramic body portions which each house a plurality of conductive terminals. The body portions are in pivoting engagement and fixed in a connector body retainer which also enables their pivoting, hinged movement. The pivoting engagement permits the ceramic body portions and terminals to hinge open to receive a gas sensor with a low insertion force and a hinge closed to provide the desired contact force.

27 Claims, 10 Drawing Sheets

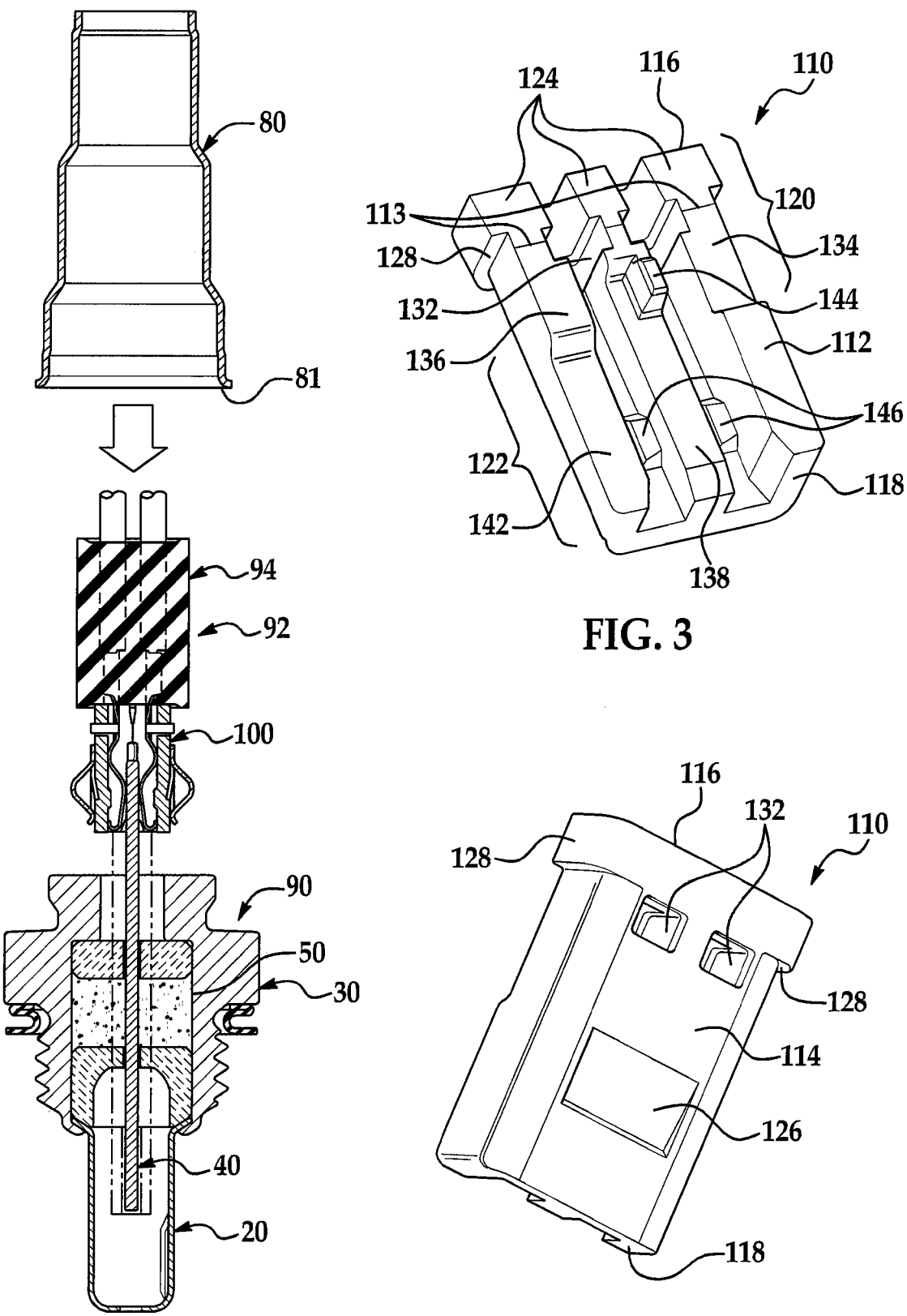

GAS SENSOR

TECHNICAL FIELD

An exemplary embodiment of the present invention relates generally to high temperature gas sensors.

BACKGROUND OF THE INVENTION

Combustion engines that run on fossil fuels generate exhaust gases. The exhaust gases typically include oxygen as well as various undesirable pollutants. Non-limiting examples of undesirable pollutants include nitrogen oxide gases (NOx), unburned hydrocarbon gases (HC), and carbon monoxide gas (CO). Various industries, including the automotive industry, use exhaust gas sensors to both qualitatively and quantitatively sense and analyze the composition of the exhaust gases for engine control, performance improvement, emission control and other purposes, such as to sense when an exhaust gas content switches from a rich to lean or lean to rich air/fuel ratio. For example, HC emissions can be reduced using sensors that can sense the composition of oxygen gas ($O_2$) in the exhaust gases for alteration and optimization of the air to fuel ratio for combustion.

A conventional high temperature gas sensor typically includes an ionically conductive solid electrolyte material, a porous electrode on the sensor's exterior exposed to the exhaust gases with a porous protective overcoat, a porous electrode on the sensor's interior surface exposed to a known gas partial pressure, an embedded resistance heater and electrical contact pads on the outer surface of the sensor to provide power and signal communication to and from the sensor. An example of a sensor used in automotive applications uses a yttria-stabilized, zirconia-based electrochemical galvanic cell with porous platinum electrodes to detect the relative amounts of oxygen present in an automobile engine's exhaust. When opposite surfaces of this galvanic cell are exposed to different oxygen partial pressures, an electromotive force (emf) is developed between the electrodes on the opposite surfaces of the electrolyte wall, according to the Nernst equation.

Exhaust sensors that include various flat-plate ceramic sensing element configurations formed of various layers of ceramic and electrolyte materials laminated and sintered together with electrical circuit and sensor traces placed between the layers, and embedded resistance heaters and electrical contact pads on the outer surface of the sensor to provide power and signal communication to and from the sensors have become increasingly popular. These flat-plate sensors generally have a sensing portion or end, that is exposed to the exhaust gases, and a reference portion or end, that is shielded from the exhaust gases providing an ambient reference. Gas sensors that employ these elements generally use high temperature electrical connectors for the electrical connection to contact pads on the reference end of the sensor to provide the necessary power and signal communication between a vehicle controller and the gas sensor. These electrical connectors are exposed to the extreme operating temperatures of internal combustion engine exhaust systems, which may include temperatures at the connector of greater than 200° C. and up to about 350° C. Thus, these connectors generally have connector bodies made from high temperature materials, such as ceramics.

These connectors also include conductive terminals which are generally disposed within the ceramic body portions and provide both contact portions to make the necessary electrical contact with the contact pads a termination portion for attachment to wires for communication with the controller. The connectors, including the ceramic body portions and terminals, must be designed so as to receive the ceramic gas sensor with a relatively low insertion force, but to have a relatively higher contact force in operation to ensure the reliability of the communications between the controller and the sensor. Various edge card connectors have been proposed for use in high temperature gas sensors. These connectors simply plug on the end of the gas sensor; however, they frequently require relatively high (e.g., greater than 2 $lb_f$ insertion forces). In these connectors, the positions of the connector bodies and terminals are fixed, and, where high temperature ceramic connector bodies are used, relatively non-resilient as compared to lower temperature connectors with polymeric connector bodies, due to the mechanical properties of the ceramics. Thus, upon insertion of the sensor, its contact pads have the full contact force of the connector terminals applied as the respective contacts slide under the terminals into the installed position. Damage to the contact pads frequently occurs; with the result that edge card connectors are generally undesirable for many gas sensor applications. One such connector has proposed a clamshell configuration where opposing halves of a ceramic connector body open in a clamshell configuration to receive the gas sensor, whereupon the halves of the sensor are closed to establish electrical contact between conductive terminals disposed on the respective connector halves and the contact pads on the gas sensor. Upon closing the connector halves, a solid metal connector retaining ring is disposed around them to retain the connector body portions and establish the operating contact force between the terminals and the contact pads.

While various high temperature electrical connector configurations have been proposed, there remains a need for improved high temperature connectors, including those having configurations which provide improved sensor insertion characteristics while maintaining sufficient contact forces after insertion, and which have designs which facilitate assembly and installation of the connector.

SUMMARY OF THE INVENTION

In general terms, this invention provides an improved high temperature gas sensor having an electrical connector with improved sensor insertion characteristics while maintaining sufficient contact forces after insertion, and which has a design configuration which facilitates assembly and installation of the connector. The invention also provides a method of assembling a gas sensor with an improved high temperature connector. The gas sensor of the invention includes a clamshell connector having a ceramic connector body and connector body retainer that has mixed characteristics of both edge card and clamshell connectors. It simply plugs on the end of the gas sensor like an edge card, but does so with a relatively low (e.g., less than 2 $lb_f$) insertion force because a clamshell configuration hinges open to receive the gas sensor, and then upon hinging closed during assembly, a relatively higher (e.g., greater than 2 $lb_f$) contact force in the fully assembled electrical connector. Sealing of the gas sensor operates to provide the contact force between the terminals of the connector and the contact pads of the sensor.

An exemplary embodiment of the invention includes a high temperature gas sensor, includes a sensor shell having an attachment portion, a sealing portion and a central bore. The sensor also includes a packing disposed in sealing and compressed engagement within the central bore. The sensor further includes a flat-plate ceramic sensor having a reference end and a sensing end, which is sealingly disposed within the packing in the central bore, the reference end extends from the sealing portion and the sensing end extends from the attachment portion, the reference end having a plurality of electrical contacts. The sensor further includes an electrical connector comprising a ceramic connector body having a pair of ceramic body portions, each having a pivot portion and a plurality of conductive terminals disposed in a sensor pocket portion, the pivot portions and sensor pocket portions disposed in opposing relation to form a sensor pocket, and a retainer having a pair of retainer bands, each having a generally U-shaped or C-shaped profile comprising a base portion and a pair of opposed extending legs, the legs of each band extending toward the other in opposing arrangement to provide the retainer, the legs of the respective bands which are in opposing arrangement are joined together by a respective pair of outwardly arched hinges opposite the sensor pocket, the conductive terminals, in signal or power communication with the electrical contacts of the sensor and the ceramic connector body disposed in the retainer; wherein the ceramic body portions are operative to pivot about the pivot portions in a hinged clamshell configuration and provide a contact force between the conductive terminal and the respective electrical contact. The sensor further includes a sealing member proximate the electrical connector disposed opposite the flat-plate sensor. The sensor further includes an upper shield having an upper shield bore, a shell end and a seal end, the shell end sealingly engaged with the sealing portion of the sensor shell, the seal end sealingly engaged with the sealing member and the electrical connector disposed within the upper shield bore. The sensor further includes a spring member disposed within the upper shield bore and biased between the upper shield member and the retainer.

The gas sensor may also include a lower shield attached to the attachment portion of the shell and disposed about the sensing end of the sensor.

The electrical connector may be configured such that the base portion of each retainer band further comprises an inwardly extending arm, and the ceramic body portions further include a retention pocket proximate the retainer and an outwardly protruding retainer flange, such that the retainer abuts the outwardly protruding retainer flange and the inwardly extending arm engages the retention pocket, whereby the position of the retainer is fixed relative to the ceramic connector body. The electrical connector may also be configured such that each retention pocket tapers inwardly. The electrical connector may also be configured such that the inwardly extending arm includes at least two inwardly extending arms on each retainer band. The electrical connector may also be configured such that each retainer band further includes an outwardly extending arm.

The electrical connector may also be configured such that the base portion of each retainer band further includes an outwardly extending arm, and the outwardly extending arms comprise the spring member. The electrical connector may also be configured such that each of the outwardly extending arms has an outwardly-bent bow shape and a free end, and may also be configured such that the free end engages the retainer surface.

The electrical connector may also be configured such that each retainer band further includes a flex member spaced from the hinges which protrudes toward the other retainer band and a retainer cavity which matingly receives the flex member of the other retainer band. The electrical connector may also be configured such that the flex member tapers inwardly from the insertion end.

The electrical connector may also be configured such that each of the terminals is disposed in a terminal channel in the respective ceramic body portion which extends into the sensor pocket, outermost terminal channels define a first end wall and a second end wall, and an inner wall is located between the first end wall and a second end wall. The electrical connector may also be configured such that the first end wall has an extension which extends above the pivot portion and the second end wall has a cavity which is recessed from the pivot portion, and wherein the respective extensions and cavities of the respective ceramic body portions engage one another. The electrical connector may also be configured such that the inner wall has an inward protruding member which is offset from a centerline of the inner wall, and wherein the respective inward protruding members of the respective ceramic body portions provide a sensor stop, and the reference end of the flat-plate ceramic sensor is proximate the sensor stop. The electrical connector may also be configured such that the inner wall has an inward protruding member which is offset from a centerline of the inner wall, and wherein the respective inward protruding members of the respective ceramic body portions provide a sensor stop, and the reference end of the flat-plate ceramic sensor is proximate the sensor stop.

The electrical connector may also be configured such that the ceramic body portions are identical.

An exemplary embodiment of the invention includes a method of making a high temperature gas sensor, including the steps of: forming a high temperature electrical connector comprising: a ceramic connector body comprising a pair of ceramic body portions, each ceramic body portion having on a side thereof a pivot portion and a sensor pocket portion, the ceramic body portions disposed with the pivot portions in touching contact and the pocket portions forming a sensor pocket; at least two conductive terminals located within the sensor pocket portion of each ceramic body portion, each terminal having a contact portion located within the sensor pocket portion and a termination portion which extends from the ceramic body portion; a retainer having a pair of retainer bands each having a generally U-shaped or C-shaped profile with a base portion and a pair of opposed extending legs, the legs of each band extending toward the other in opposing arrangement to provide the retainer, legs of the respective bands which are in opposing arrangement are joined together by a respective pair of outwardly arched hinges; the ceramic connector body disposed in the retainer, wherein the ceramic body portions are operative to hinge open about the hinges and pivot portions to a clamshell configuration; inserting a flat-plate ceramic sensor having a plurality of electrical contacts into the sensor pocket, whereby the ceramic body portions hinge open to receive the sensor; disposing an upper shield about the electrical connector and flat-plate ceramic sensor; and biasing a spring member between the upper shield and the electrical connector so as to apply a predetermined normal contact force between each conductive terminal and the respective electrical contact sufficient to establish power or signal communication between them.

The method may also include a step of forming a sensor subassembly incorporating the flat-plate ceramic sensor prior to the step of inserting the sensor into the electrical connector, the sensor assembly comprising a sensor shell having an attachment portion, a sealing portion and a central bore; a packing disposed in sealing and compressed engagement within the central bore; and the flat-plate ceramic sensor having a reference end and a sensing end, which is sealingly disposed within the packing in the central bore, the reference end extends from the sealing portion and the sensing end extends from the attachment portion, the reference end having the plurality of electrical contacts.

The method may provide that each of the retainer bands includes an outwardly extending arm, wherein the step of biasing comprises crimping the upper shield to compress the outwardly extending arm.

The method may also provide that the predetermined contact force produced by crimping is at least 2 $lb_f$.

The method may also provide that each of the retainer bands comprises an outwardly extending arm, wherein the step of biasing includes crimping the upper shield to compress the outwardly extending arm. The method may also provide that the upper shield further includes a seal end and a shell end, the gas sensor further includes a seal proximate the electrical connector disposed in the seal end of the upper shield, the sealing portion of the shell is disposed in the shell end of the upper shield, and crimping further includes deforming the upper shield to form a first sealed joint between the seal and the upper shield and a second sealed joint between the shell and the upper shield.

The method may also include a step of attaching a lower shield to the attachment portion of the shell.

The method may also provide that each of the terminals is disposed in a terminal channel in the respective ceramic body portion which extends into the sensor pocket and each of the conductive terminals has an inwardly-bent bow portion and the contact portion is proximate an apex of the inwardly-bent bow. The method may also provide that each of the outwardly extending arms has an outwardly extending bow portion and the upper shield is compressed against an apex of each outwardly extending bow. The method may also provide that lines of normal force between the terminals and the electrical contacts and lines of normal force between the outwardly extending arms upper shield are substantially co-planar.

BRIEF DESCRIPTION OF THE DRAWINGS

The following is a brief description of the drawings wherein like elements are numbered alike in the several views:

FIG. 2 is a schematic cross-sectional view illustrating the insertion of a precursor upper shield onto a sensor-connector subassembly;

FIG. 3 is an front perspective view of an exemplary embodiment of a connector body;

FIG. 4 is an rear perspective view of the connector body portion of FIG. 3;

DETAILED DESCRIPTION OF A PREFERRED EMBODIMENT

Figure 1:
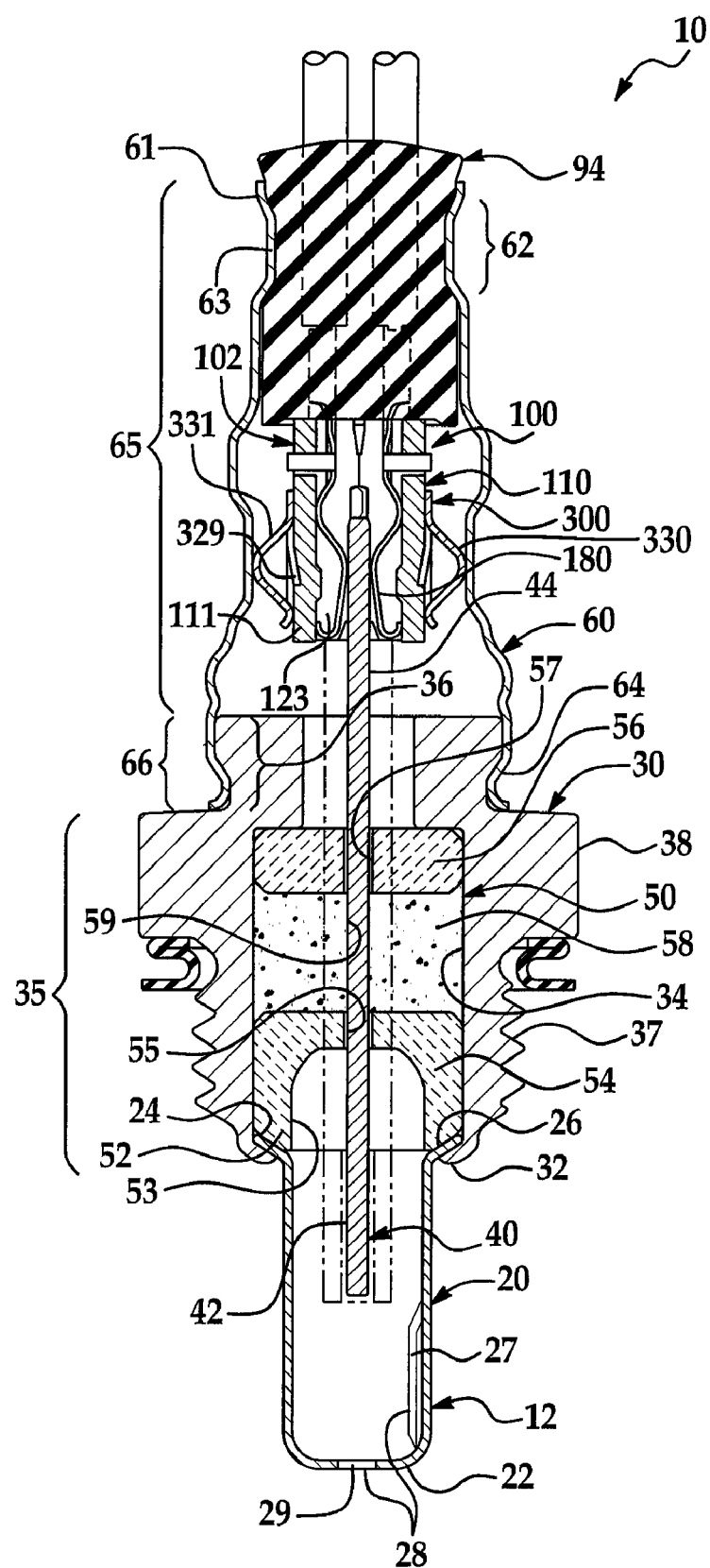
FIG. 1 is a cross-sectional view of an exemplary embodiment of high temperature connector according to the invention in a high temperature gas sensor.

An exemplary embodiment of the present invention provides an improved high temperature gas sensor having a high temperature electrical connector. The electrical connector incorporates a ceramic connector body having a pair of opposing ceramic body portions which each house a plurality of conductive terminals. The body portions are in pivoting engagement and fixed in a connector body retainer which also enables their pivoting, hinged movement. The pivoting engagement permits the ceramic body portions and terminals to hinge open to receive a gas sensor with a low insertion force and a hinge closed to provide the desired contact force. The ceramic body portions may also include a taper section in a pivot portion with a taper angle that may be varied to control the pivoting, hinged movement of the electrical connector. The ceramic body portions may also include a retention pocket proximate to the connector body retainer for cooperation with outwardly extending arms of the retainer, as well as a protruding flange, for retention of the body portions in the retainer. The ceramic body portions may also include channels and associated bores for housing and retention of the conductive terminals, as well as features to assist in alignment of the of the gas sensor during insertion. A particular advantage of the gas sensor is that the compact high temperature electrical connector and other aspects described herein enable more compact gas sensors, including those having an M12× 1.25 thread form, 14 mm wrench flats and an overall length of about 46.5 mm, a smaller lower shield having a diameter of only about 5.3 mm and protruding length of about 10.5 mm and a smaller sensor element having a width of about 2.4 mm, a length of about 27 mm and a thickness of about 0.82 mm. This small overall gas sensor profile provides much more flexibility in the mounting of the sensor, including access to various manifolds, conduits and other mounting points which were previously too small in themselves, or inaccessible due to the larger envelope of free space required to place or attach larger sensors due to the interference constraints associated with other vehicle or engine components. The reduced profile also provides a benefit with regard to material cost savings due to the reduced amounts of material required for most of the sensor components. The smaller thread size also enables mounting the sensors in smaller diameter and smaller length exhaust pipes and other conduits. Further, the smaller cross-section of the lower shield and sensing end of the sensor reduces intrusion into and interference with the exhaust stream. Still further, the smaller gas sensor houses a much smaller flat-plate ceramic sensing element that requires less power for activation (burn-off) of the sensor and a shorter sensor response times, thereby reducing the power load on the electrical systems and improving the responsiveness of the vehicle emission control systems of vehicles which utilize these sensors.

FIG. 1 illustrates a high-temperature gas sensor 10 which is adapted to qualitatively and quantitatively sense various exhaust gases, such as $O_2$, $NO_X$, HC, CO and the like, which incorporates an exemplary embodiment of the connector retainer body of the present invention. An exemplary embodiment of gas sensor 10 includes a generally cylindrical lower shield 20, sensor shell 30, flat-plate ceramic sensor 40, sensor packing 50, upper shield 60 and electrical connector assembly 100. Gas sensor 10 is suitable for exposure in a high temperature exhaust gas stream, including operating temperatures up to about 1000° C. at the sensing end 12 that is located in the exhaust gas stream, such as those found in the exhaust system of an internal combustion engine, including those used in many vehicular applications. Gas sensor 10 may be made in a compact form with an overall length of about 46.5 mm from the lower end of the lower shield to the upper end of the elastomeric seal.

Lower shield 20 is a substantially cylindrical form having a substantially closed end 22 and an open end 24. Open end 24 may include an outwardly extending flange 26 in the form of a straight taper or arcuate flair or other suitable flange form. Lower shield 20 is preferably formed of a metal that is adapted for high-temperature performance including resistance to high temperature oxidation and corrosion, particularly as found in high temperature exhaust gases and corrosive combustion exhaust byproducts associated with the exhaust stream of an internal combustion engine. Suitable metals include various ferrous alloys, such as stainless steels, including high chrome stainless steel, high nickel stainless steel, as well as various Fe-base, Ni-base, and Cr-base superalloys. The various ferrous and other alloys described above are generally indicative of a wide number of metal alloys that are suitable for use as lower shield 20. In an exemplary embodiment, lower shield 20 may be formed from type 310 stainless steel (UNS 31008) and may have an outer diameter of about 5.3 mm and an exposed length (i.e., below the deformed shoulder 32) of about 10.5 mm. Lower shield 20 abuts a lower end 52 of packing 50 and applies a compressive force thereto by the operation of deformed shoulder 32 at a lower end of shell 30. Deformed shoulder 32 presses against the outer surface of outwardly extending flange 26 and acts to retain both lower shield 20 and packing 50 within central bore 34 of shell 30. Lower shield 20 also includes one or more orifices 28 in the form of a bore 29, or louver 27 formed by piercing and inwardly bending the sidewall. Bore 29 may have any suitable shape, including various cylindrical, elliptical and slot-like shapes. Orifices 28 permit exhaust gases to enter the interior of lower shield 20 and come into contact with the lower or sensing end 42 of sensor 40 during operation of sensor 10, while at the same time, lower shield 20 provides a physical shield for sensor 40 against damage from the full fluid force of the exhaust gas stream, or from damage that may be caused by various mechanical or thermal stresses that result during installation or operation of sensor 10. While deformed shoulder 32 is illustrated for attachment of lower shield 20 in compressive engagement with packing 50, it will be appreciated that other means of attaching lower shield 20 to shell 30 while maintaining packing 50 in compressed engagement are possible, including various forms of weld joints, brazed joints and other attachment means and mechanisms.

In addition to deformed shoulder 32 and central bore 34, sensor shell 30 may be described generally as having an attachment portion 35 and a sealing portion 36. Attachment portion 35 may include a threaded form 37 which is adapted for threaded insertion and attachment into a component of the exhaust system of an internal combustion engine, such as an exhaust manifold or other exhaust system component, and tool attachment features 38, such as various forms of wrench flats (e.g. hex-shaped, double-hex and other wrench flat configurations). In an exemplary embodiment, shell 30 may have a thread form of M12×1.25 and a 14 mm hex wrench flats and be formed from Ni-plated steel. Shell 30 may be made from any material suitable for high-temperature exposure, including installation stresses associated with the threaded connection, mechanical stresses associated with usage of the device including various bending moments, thermal stresses and the like. Shell 30 will preferably be formed from a ferrous material, such as various grades of steel, including various plated or coated steels, such as those having various pure nickel or nickel alloy plating or coatings; however, the use of other metal alloys is also possible. While one embodiment of shell 30 is described herein, it will be appreciated by one of ordinary skill that many other forms of shell 30 may be used in conjunction with the present invention.

Referring again to FIG. 1, packing 50 is made up of a lower support disk 54, an upper support disk 56 and sealing member 58. Lower support disk 54 has a central slot 55 that is adapted to receive sensor 40 in closely spaced relation between slot 55 and the outer surface of sensor 40 proximate to slot 55. Generally, a substantially rectangular slot configuration provides closely spaced relation between lower support disk 54 and the outer surface of sensor 40. Lower support disk 54 may have a relieved portion 53 to provide spacing from sensor 40, and increase the exposure of the surface of sensor 40 to the exhaust gases that enter the interior of lower shield 20 during operation of sensor 10 in conjunction with operation of the associated internal combustion engine. Lower support disk 54 will generally be sized for slip-fit engagement with central bore 34 such that lower support disk 54 may be inserted into central bore 34 during assembly and yet have a minimal gap therebetween so as to reduce the tendency for leakage of exhaust gas between the outer surface of lower support disk 54 during operation of the sensor 10. The lower end 52 of the lower support disk 54 and central bore 34 may be tapered downwardly and inwardly or otherwise adapted for mating engagement with flange 26. Lower support disk 54 will generally be made from an electrically and thermally insulating, high-temperature ceramic material. Any suitable high-temperature ceramic material may be utilized, including various oxide, nitride or carbide ceramics or combinations thereof. Any suitable material may be utilized which is compatible with the function of sensor 40 and the operation of sealing member 58 in the high temperature operating environment of sensor 10.

The upper end of lower support disk 54 compressively engages sealing member 58. Sealing member 58 is preferably a compressed insulating powder, such as a talc disk. The compressed powder material of sealing member 58 is both electrically and thermally insulating. Sealing member 58 also has a central slot 59 that is adapted to receive sensor 40 in closely spaced relation between slot 59 and the outer surface of sensor 40 proximate to slot 59, particularly during installation of sealing member 58 over sensor 40. Upon installation of packing 50, including the compressive loading described herein, sealing member 58 is in compressed sealing engagement with the sensor 40 on the interior thereof, and shell 30 on the exterior thereof. Upon compressive installation of packing 50, sealing member 58 is operative to prevent passage of hot exhaust gases, particularly those received through orifices 28, from passing between the packing 50 and central bore 34 or along the surface of sensor 40 to an upper end 44 thereof.

Upper support disk 56 is in pressing engagement with sealing member 58 and is adapted to retain sealing member 58, such as by preventing it from being extruded through an upper portion of central bore 34. Upper support disk 56 also includes a central slot 57 that is adapted to receive sensor 40 in a similar manner as central slot 55 of lower support disk 54. Upper support disk 56 is likewise adapted for slip-fit engagement with central bore 34 in the manner described for lower support disk 54. Upper support disk 56 may be made from any suitable high temperature material, including ceramics or other materials identical to those used for lower support disk 54. However, upper support disk may also be made from a separate material, including a different ceramic material than that of lower support disk 54. Since upper support disk 56 is located further from the exhaust gas stream than lower support disk 54 and generally is exposed to somewhat lower temperatures than lower support disk 54, it may be desirable in some applications to make upper support disk 56 from a different material than that of lower support disk 54. While one configuration of packing 50 has been described, it will be appreciated that many other forms of packing 50 may be used in conjunction with the present invention.

High temperature gas sensor 40 may be of any suitable internal and external configuration and construction. Gas sensor 40, is preferably a flat-plate sensor having the shape of a rectangular plate or prism. Gas sensor 40 will typically include an ionically conductive solid electrolyte material, a porous electrode on the sensors exterior which is exposed to the exhaust gases, a porous protective overcoat, a porous electrode on the interior of the sensor which is adapted for exposure to a known gas partial pressure, an embedded resistance heater and various electrical contact pads on the outer surface of the sensor to provide the necessary circuit paths for power and signal communication to and from the sensor. Depending on the arrangement of the various elements described above, gas sensor may be configured to quantitatively, qualitatively, or both, sense various constituents of the exhaust gas, including $O_2$, $NO_X$, HC and CO. For automotive applications, an example of a suitable construction of sensor 40 would include a yttria-stabilized, zirconia-based electrochemical galvanic cell with porous platinum electrodes to detect the relative amounts of oxygen present in engine exhaust. When opposite surfaces of such a galvanic cell located at sensing end 42 and reference end 44 are exposed to different oxygen partial pressures, an electromotive force (emf) is developed between electrodes located at these ends on the opposite surfaces of the electrolyte wall according to the Nernst Equation. In an exemplary embodiment, gas sensor may have the shape of a rectangular prism having a width of about 2.4 mm, a length of about 27 mm and a width of about 0.82 mm. While an exemplary embodiment of gas sensor 40 is described above, various configurations of gas sensor 40 are contemplated for use in conjunction with the exemplary embodiment of the invention, including gas sensors 40 which are adapted for sensing other exhaust gas constituents, and further including gas sensors having other dimensions and flat-plate configurations.

Figure 20A:
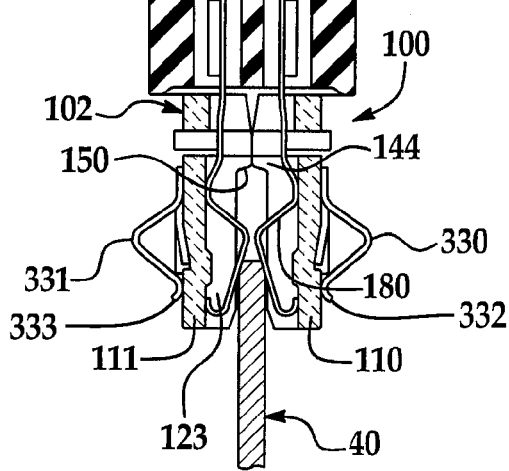
FIGS. 20A-20D are a schematic cross-sectional illustration of insertion of a gas sensor subassembly and gas sensor into an electrical connector of the invention.
Figure 20B:
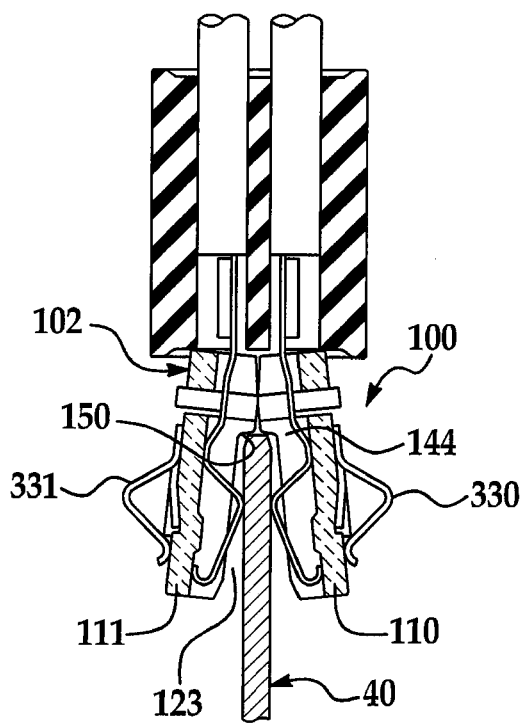
Figure 20C:
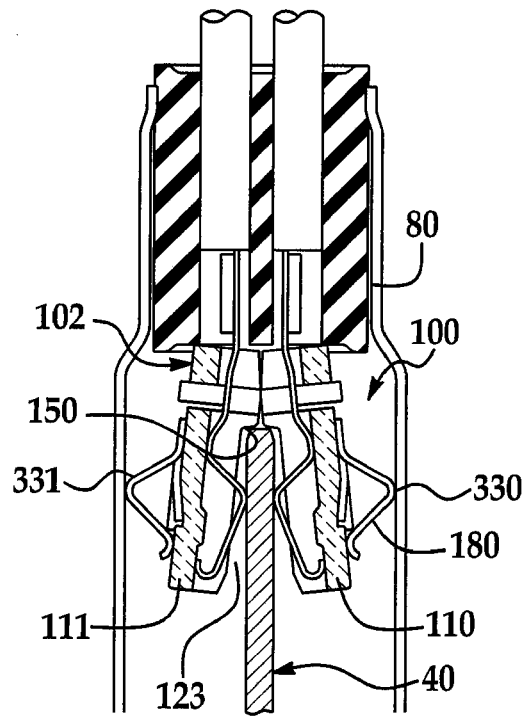
Figure 20D:
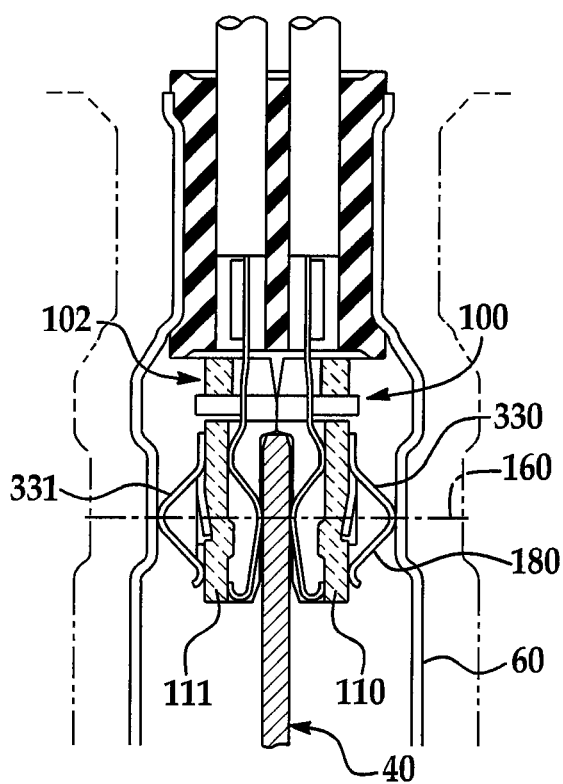

Referring to FIG. 2, in an exemplary embodiment, the lower shield 20, sensor shell 30, gas sensor 40 and packing 50 may be assembled in the manner described herein to form a sensor subassembly 90. The electrical connector 100 is inserted onto the sensor subassembly 90 by insertion of the upper or reference end 44 of sensor 40 into a sensor pocket on the insertion end of electrical connector 100, as shown in FIG. 2, to form a sensor/connector subassembly 92. As shown in FIG. 20A, electrical connector 100 hinges open to receive sensor 40 of sensor subassembly 90. Referring to FIG. 20B, a relatively low insertion force, less than about 2 $lb_f$, is realized as sensor 40 moves from the position shown in FIG. 20A to the position shown in FIG. 20B. It will be appreciated that the insertion force may be resolved as a normal (to the sensor surface) force vector and an orthogonal force vector associated with the sliding friction between the terminal and substrate surface. At the position shown in FIG. 20B, sensor 40 rests against protruding members 144 and sensor stop surface 150. At the position shown in FIG. 20B, various tests may be conducted to verify sufficiently low resistance of the electrical contacts between sensor 40 and terminals 180 for signal and power communication therebetween prior to enclosing the sensor subassembly 90 with precursor upper shield 80 as shown in FIG. 20C. Alternately, the testing described may be done after the precursor upper shield 80 encloses the sensor subassembly 90, or at both stages. FIG. 20D illustrates the use of the crimp die shown in phantom used to crimp precursor upper shield to form upper shield 60 and establish the final working contact force of the conductive terminals of the electrical connector against the respective contact pads on the sensor (not shown). The final working contact force is preferably larger, for example, greater than about 2 $lb_f$. It will be appreciated that the contact force is essentially a normal (to the sensor surface) force vector. It is preferred that sensor 40 and electrical connector 100 be configured so that upon insertion of the sensor subassembly 90, sufficient power and signal communication are established between the conductive terminals 180 of the electrical connector 100 and the electrical contacts (not shown) of sensor 40 to pretest the electrical connections between them. Once the necessary electrical connections are assured, the assembly of gas sensor 10 is completed by the addition of upper shield of 60 which is formed from the precursor upper shield 80, as shown in FIG. 2.

Figure 6:
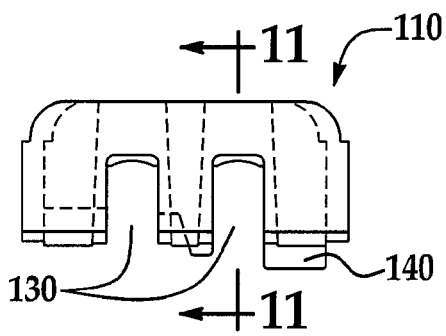
FIG. 6 is a top view of the connector body portion of FIG. 3.
Figure 7:
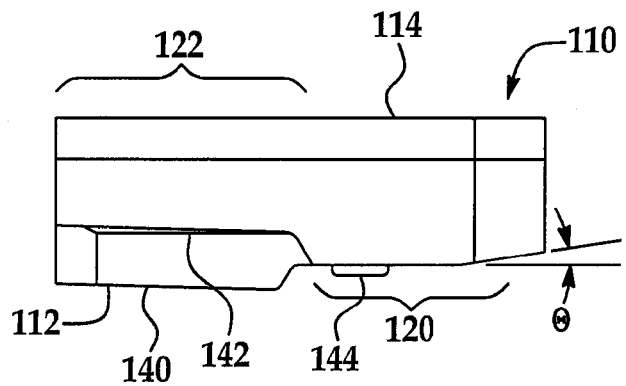
FIG. 7 is a left side elevational view of the connector body of FIG. 3.

Referring again to FIG. 2, the precursor upper shield 80 is installed over the sensor-connector subassembly 92 (FIG. 6) to the position shown in FIG. 7 so that the upper end 81 of precursor upper shield is located proximate, preferably in touching contact with, an upper shoulder of tool attachment feature 38. Precursor upper shield 80 is preferably formed of a metal that is adapted for high-temperature performance including resistance to high temperature oxidation and corrosion, particularly as found in high temperature exhaust gases and corrosive combustion exhaust byproducts associated with the exhaust stream of an internal combustion engine. Suitable metals include various ferrous alloys, such as stainless steels, including high chrome stainless steel, high nickel stainless steel, as well as various Fe-base, Ni-base, and Cr-base superalloys. The various ferrous and other alloys described above are generally indicative of a wide number of metal alloys that are suitable for use as precursor upper shield 80. In an exemplary embodiment, precursor upper shield 80 may be formed from type 304 stainless steel (UNS 30400). In an exemplary embodiment, precursor upper shield 80 may have an overall length of about 22 mm and an inner diameter that varies in three cylindrical sections of decreasing diameter from top to bottom of about 7 mm to about 11 mm. The precursor upper shield 80 is deformed, such as by crimping, to form upper shield 60.

Upper shield 60 is formed from a precursor upper shield 80, such as that shown in FIG. 2. A gas-tight upper sealed joint 62 is formed in sensor 10 when precursor upper shield 80 as shown in FIG. 2 is plastically deformed into upper shield 60 having the shape shown in FIG. 1. This deformation may include a plurality of crimps formed along the length of precursor upper shield 80. A gas-tight upper sealed joint 62 is formed when precursor upper shield 80 as shown in FIG. 2 is crimped and plastically deformed into upper shield 60 having the shape shown in FIG. 1. Crimp 63 provides pressing engagement between an inner surface of the upper end of upper shield 60 and an outer surface of elastomeric sealing member 94. Crimp 63 deforms precursor upper shield 80 at an upper end 82 thereof sufficiently to provide pressing engagement between upper shield 60 and elastomeric sealing member 94, including the deformation of elastomeric sealing member 94, thereby forming upper sealed joint 62. While shown as a single radial crimp 63 in FIG. 1, upper sealed joint 62 may also be formed by a plurality of radial crimps of the type described herein. Upper shield 60 has a shell portion 66 and a connector portion 65 that extends upwardly and away from shell 30 and generally includes the portions of upper shield 60 other than shell portion 66.

Sensor 10 also includes a lower sealed joint 64 between sealing portion 36 of shell 30 and the shell portion 66 of upper shield 60. Referring now to FIG. 1, lower sealed joint 64 is a gas-tight sealed joint formed between the outer surface of sealing portion 36 of shell 30 and the inner surface of the shell portion 66 of upper shield 60. Lower sealed joint 64 is formed when precursor upper shield 80 is crimped and plastically deformed into upper shield 60 having the shape shown in FIG. 1.

Referring again to FIG. 1, electrical connector 100 is adapted to provide an electrical connection for power and signal communication between sensor 40 and a device that is adapted to receive such communications, such as an engine or other controller while at the same time providing the required electrical isolation between the various circuit paths associated with the required power and signal communication. Electrical connector 100 is in spring-biased engagement within an upper end 61 of upper shield 60 through outwardly extending spring arms 330, 331 associated with the connector body retainer 300. Electrical connector 100 is a clamshell configuration of a ceramic connector body 102 which includes of a pair of ceramic connector body portions 110,111 that are housed and retained in connector body retainer 300. The spring-bias closes the clamshell and ensures a sufficient contact pressure between the conductive terminals 180 of the connector and electrical contacts (not shown) located on the upper end 44 of sensor 40 to provide a low resistance electrical connection sufficient for signal and power communication between sensor 40 and a device, such as a controller, which is adapted to receive the signal.

Figure 9:
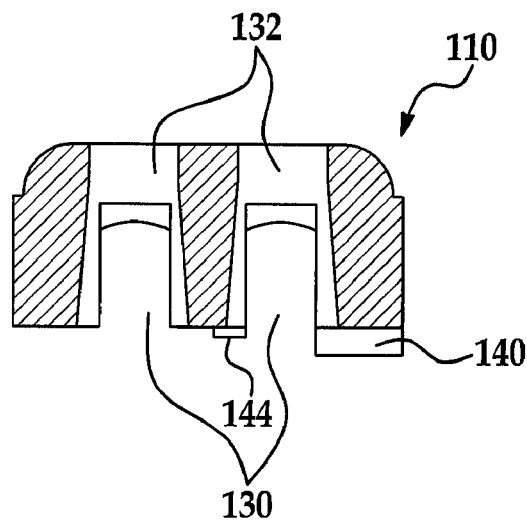
FIG. 9 is a cross-section of the connector body portion of FIG. 3 taken along Section 9-9.
Figure 10:
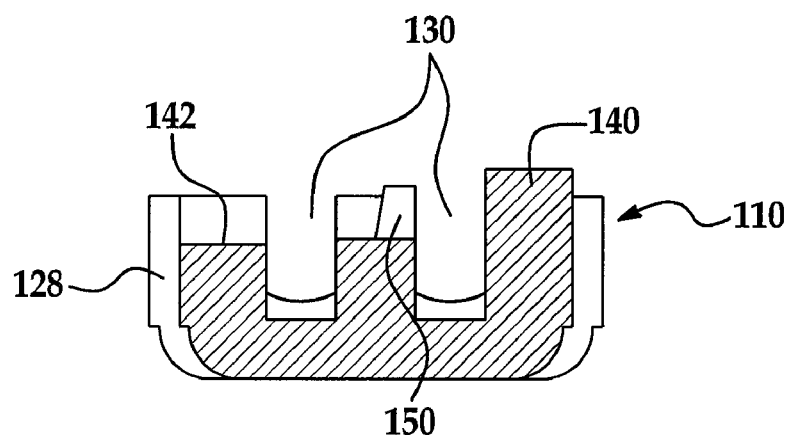
FIG. 10 is a cross-section of the connector body portion of FIG. 3 taken along Section 10-10.

Referring to FIGS. 1-2, an exemplary embodiment of the present invention provides a connector body 102. Ceramic connector body 102 provides a suitable structure for housing conductive terminals 180. It provides a physical structure for attachment and positioning of conductive terminals 180, as well as providing electrical isolation between them. Ceramic connector body 102 cooperates with conductive terminals 180, as well as connector body retainer 300 to provide electrical contact to gas sensor 40 for power and signal communication between the sensor and a controller (not shown). Ceramic connector body 102 may have, and ceramic body portions 110,111 may be configured to provide, a substantially rectangular outer profile or cross-section, as may be understood from the partial profile that is shown, for example, in FIGS. 6 and 9, where, but for the rounded corners, the full body profile is substantially rectangular. In this embodiment, ceramic connector body 102 has the shape of a substantially rectangular prism. It is believed that ceramic connector body 102 may have, and ceramic body portions 110 may also be configured to provide, other shapes, including a substantially circular outer profile or cross-section (not shown). This would provide a ceramic connector body 102 with the shape of a cylinder. The ceramic connector body 102 may further be configured to have a non-square, substantially rectangular outer profile or cross-section. This configuration is advantageous in that it greatly reduces or eliminates the possibility of mis-orientation of the ceramic connector body 102 within the connector body retainer 300 during their assembly.

Referring to FIGS. 1-11, 15 and 16, the ceramic connector body 102 includes a pair of ceramic body portions 110,111 (as shown in FIGS. 1 and 2). Body portions 110 may have an identical configuration; however, the various features of body portions 110 described herein may also be incorporated in non-identical body portion configurations. Since the body portions are identical in the exemplary embodiments described herein, except for FIGS. 1 and 2, reference is made only with respect to body portion 110. Ceramic body portions 110 may be made from any suitable ceramic material. In an exemplary embodiment, ceramic body portions 110 may be made from steatite. Ceramic body portions 110 may be made using any suitable method for forming them, including the various body features described herein, such as various molding and sintering methods.

Each body portion 110 has a terminal side 112 and a retainer side 114. Terminal side 112 is the side on which the terminals are housed. Retainer side 114 is the side which faces connector body retainer 300. Each body portion 110 also has a terminal end 116 and a connection end 118. Terminal end 116 is the end through which terminals extend for interconnection with wires (see FIGS. 1 and 2) used to provide signal and power communication with a controller. Connection end 118 is the end that faces the gas sensor 40.

Terminal side 112 has a pivot portion 120 and a sensor pocket portion 122. The pivot portions 120 and sensor pocket portions 122 of a given pair of body portions 110 are adapted for disposition in opposing relation. In this opposing relation, the sensor pocket portions 122 provide a sensor pocket 123 between them and the pivot portions 120 are in touching contact, as illustrated in FIGS. 1 and 2. The sensor pocket 123, and sensor pocket portions 122, are designed with regard to size and shape so as to be operative to receive the reference end of gas sensor 40. The pivot portions 120 are configured such that they are operative for pivoting engagement (as shown in FIGS. 1 and 2) to enable the electrical connector to hinge open and hinge closed in the manner described herein. Pivot portion 120 may comprise a flat planar structure, and may include a plurality of intersecting flat planes as shown, for example, in FIG. 3, where opposing body portions 110 pivot generally about the line 113 formed by the intersection of the planes. However, it is believed that alternate structures of the pivot portion 120, for example, such as one having an arcuate region where the flat planes intersect, or one having an inwardly convex (convex in the direction of the mid-plane) curvature, would also work in accordance with the invention described herein. The pivot portion 120 may include a tapered section 124 and a taper angle ($\theta$), as shown, for example, in FIGS. 3, 5 and 7. Ceramic connector body portions 110 may also be configured such that the taper angle is at least 5°. The taper angle (θ) may be selected to provide the desired degree of hinged opening of the ceramic connector body 102 within connector body retainer 300 for insertion of gas sensor 40.

Figure 8:
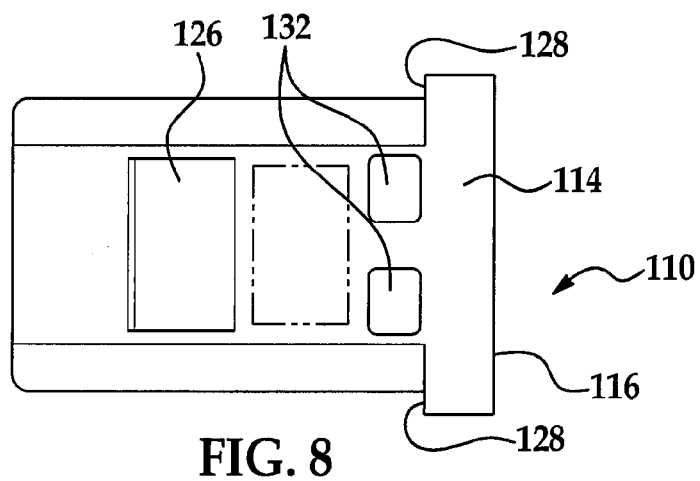
FIG. 8 is a rear view of the connector body portion of FIG. 3
Figure 11:
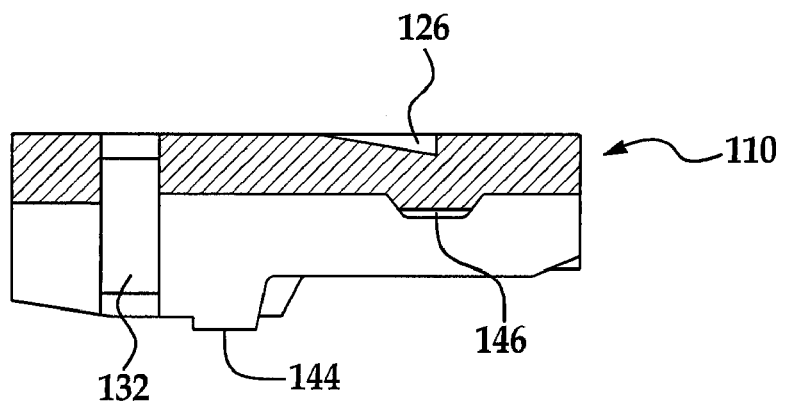
FIG. 11 is a cross-section of the connector body portion of FIG. 6 taken along Section 11-11.
Figure 12:
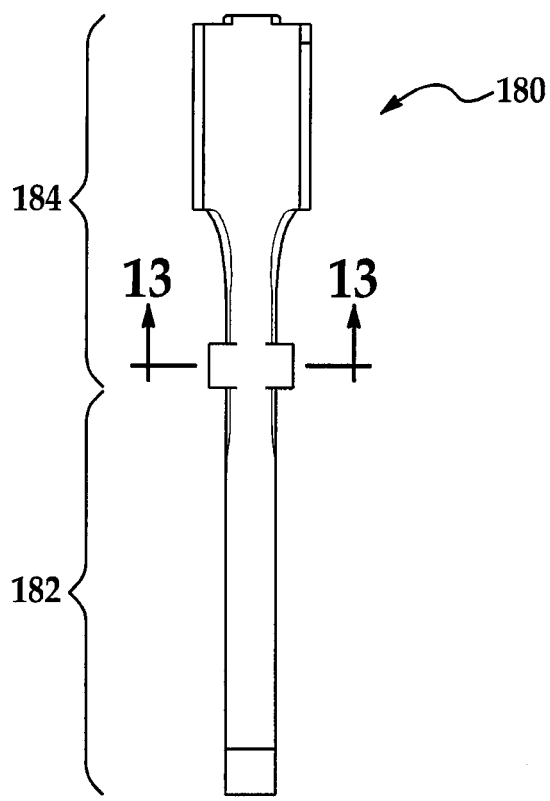
FIG. 12 is a front view of an conductive terminal.
Figure 13:
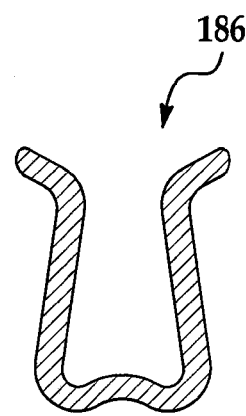
FIG. 13 is a cross-sectional view of the conductive terminal of FIG. 12 taken along Section 13-13.
Figure 14:
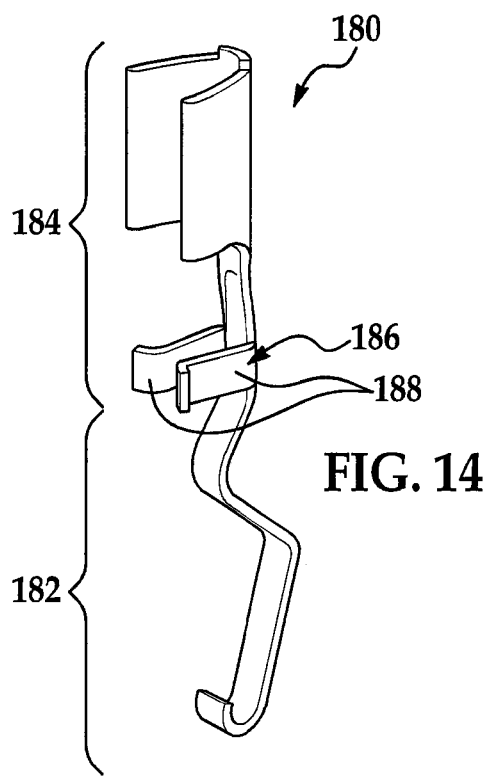
FIG. 14 is a front perspective view of the conductive terminal of FIG. 12.
Figure 23:
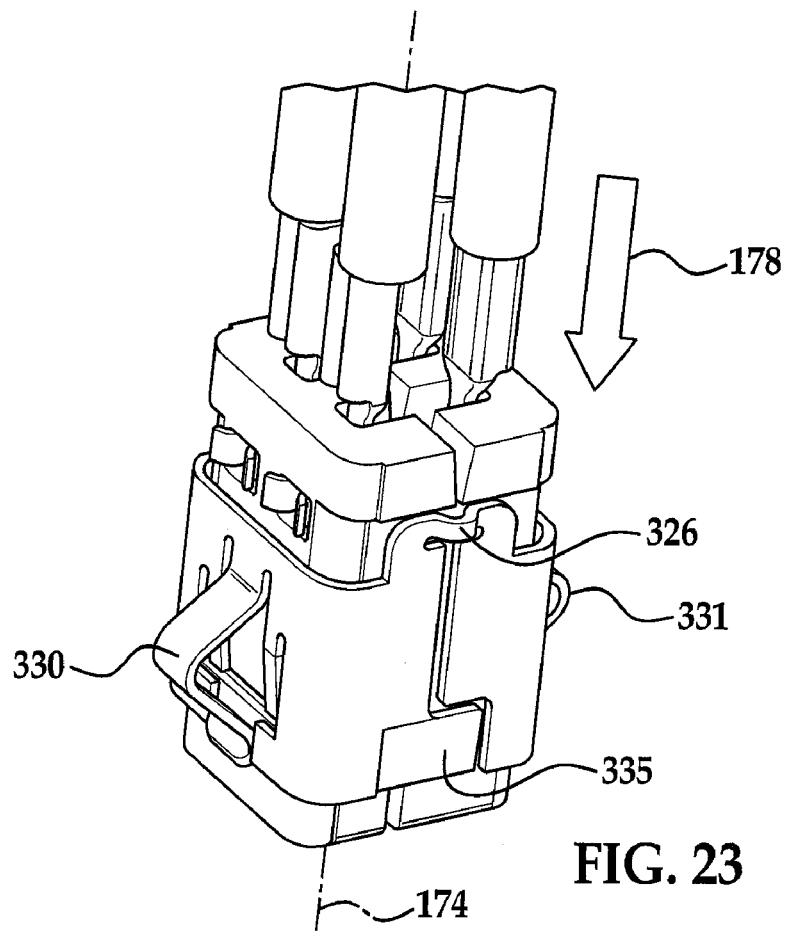
FIG. 23 is a perspective view of the electrical connector of FIG. 21 from the connection end in a hinged close position.

Referring to FIGS. 4, 8 and 11, ceramic connector body portions 110 may also be configured to include a retention pocket 126 in the retainer side 114 and an outwardly protruding retainer flange 128 proximate one of the terminal end 116 or the connection end 118. Retention pocket 126 may have any suitable shape and configuration. Retention pocket 126 may be shaped so as to permit the capture of inwardly extending arms 328,329 of connector body retainer 300 upon insertion of ceramic connector body 102 and body portions 110 therein, as shown, for example, in FIGS. 1, 2 and 23. Retention pockets 126 may be configured to taper inwardly away from the retainer flange 128, as shown in FIGS. 4 and 8. As also shown in FIGS. 4 and 8, retainer flanges 128 are located proximate terminal ends 116. Retainer flanges 128 are configured to abut hinge ends 322,323 of connector body retainer 300. As shown in FIGS. 1, 2 and 23, the retention pockets 126 and retainer flanges cooperate with the respective features of connector body retainer 300 described above to capture ceramic connector body portions 110 in retainer 300. It is believed that retainer flanges 128 may be located proximate either the terminal end 116 or the connection end 118, with respective suitable rearrangement of the orientation of retention pockets 126 and retainer 300.

Ceramic connector body portions 110 may also be configured to include a plurality of terminal channels 130 disposed between the terminal end 116 and the connection end 118 which extend into the sensor pocket 124. As shown in FIGS. 15, 16 and 21-24, the plurality of terminal channels 130 are adapted house and retain a corresponding plurality of electrical terminals 180 within the terminal channels 130 in electrical isolation from all non-associated conductive terminals. Only two channels are illustrated; however, any number of additional channels may be incorporated to house additional terminals, such 3, 4, 5, 6 or more terminal configurations.

Figure 15:
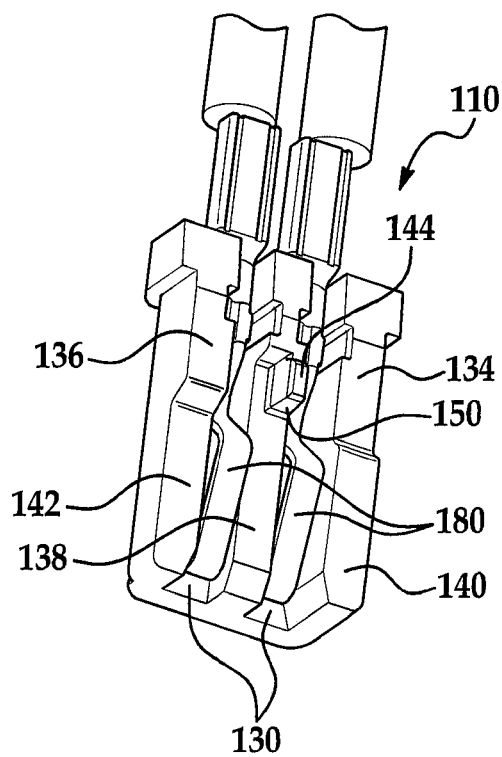
FIG. 15 is a front perspective view of a connector body and conductive terminal assembly.
Figure 16:
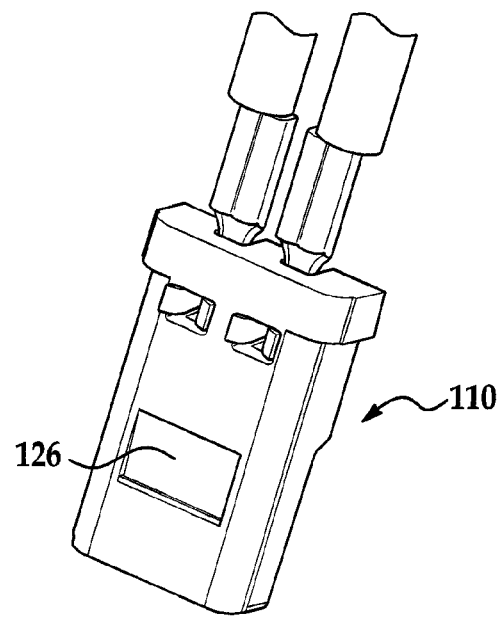
FIG. 16 is a rear perspective view of the connector body and conductive terminal assembly of FIG. 16.

Referring to FIGS. 12-16, electrical or conductive terminals 180 have a contact portion 182 and a termination portion 184. Any suitable configuration of conductive terminal 180 may be used. In an exemplary embodiment, contact portion 182 has an inwardly-bent bow configuration. The inwardly-bent bow configuration of contact portion 182 acts as a spring member upon hinged closure of the electrical connector against the gas sensor in the manner shown in FIGS. 1 and 2 to establish a spring bias electrical contact with contact pads of the gas sensor and provide a sufficient contact force to establish and ensure reliable signal and power communication between the sensor and a controller. As shown in FIG. 20D, the line of contact force acts substantially along a contact axis 160 which passes through the apex of outwardly extending arms 330,331 and the apex of the bow shaped terminals 180. This configuration of outwardly extending arms 330,331 and bow shaped terminals 180 is particularly advantageous as it minimizes or eliminates bending moments in gas sensor 40, thus, reducing the possibility of damage to sensor 40 during installation or operation of gas sensor 10. The termination portion 184 also includes an attachment tang 186. In an exemplary embodiment, attachment tang 186 is substantially U-shaped with a pair of inwardly arched legs 188. The inwardly arched legs 188 may be compressed as a spring member in conjunction with insertion in a terminal bore 132, such that upon full insertion, the legs 188 flex outwardly over an outer edge of the bore, thereby capturing tang 186 in terminal bore 132 and conductive terminal 180 within terminal channel 130, as shown in FIGS. 15 and 16. Conductive terminals 180 may be made from any suitable conductive material. In an exemplary embodiment, conductive terminals 180 are made from stainless steel, with a coating of a conductive material, such as gold, having better electrical conductivity than stainless steel and high temperature oxidation and corrosion resistance.

Referring, for example, to FIGS. 1, 2, 5 and 8, ceramic connector body portions 110 may also be configured such that each terminal channel 130 has a terminal bore 132 which extends from terminal channel 130 through ceramic body portion 110 and provides an opening in retainer side 114.

Figure 5:
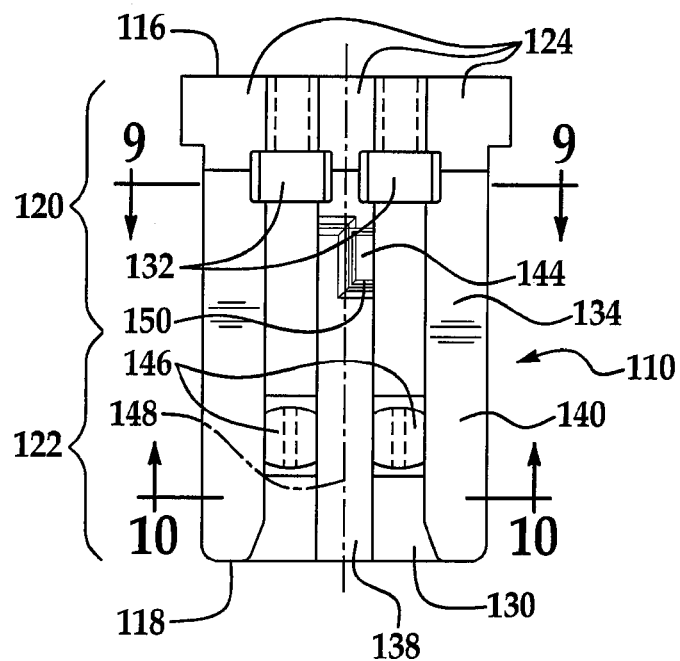
FIG. 5 is a front view of the connector body portion of FIG. 3.
Figure 21:
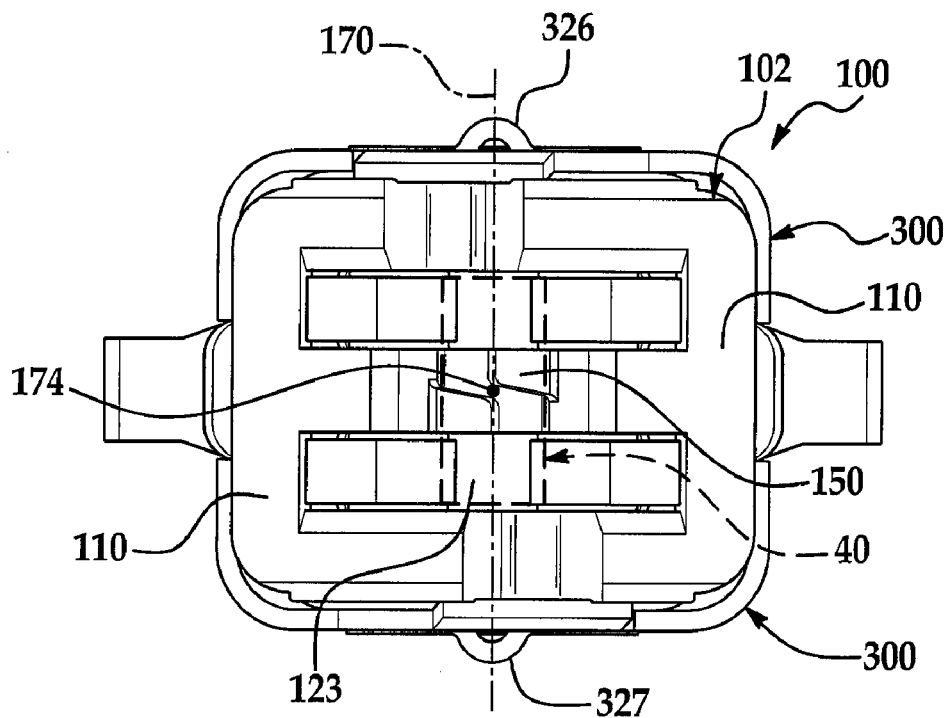
FIG. 21 is a top view of an electrical connector in accordance with an exemplary embodiment of the present invention from the insertion end in a hinged open position.
Figure 24:
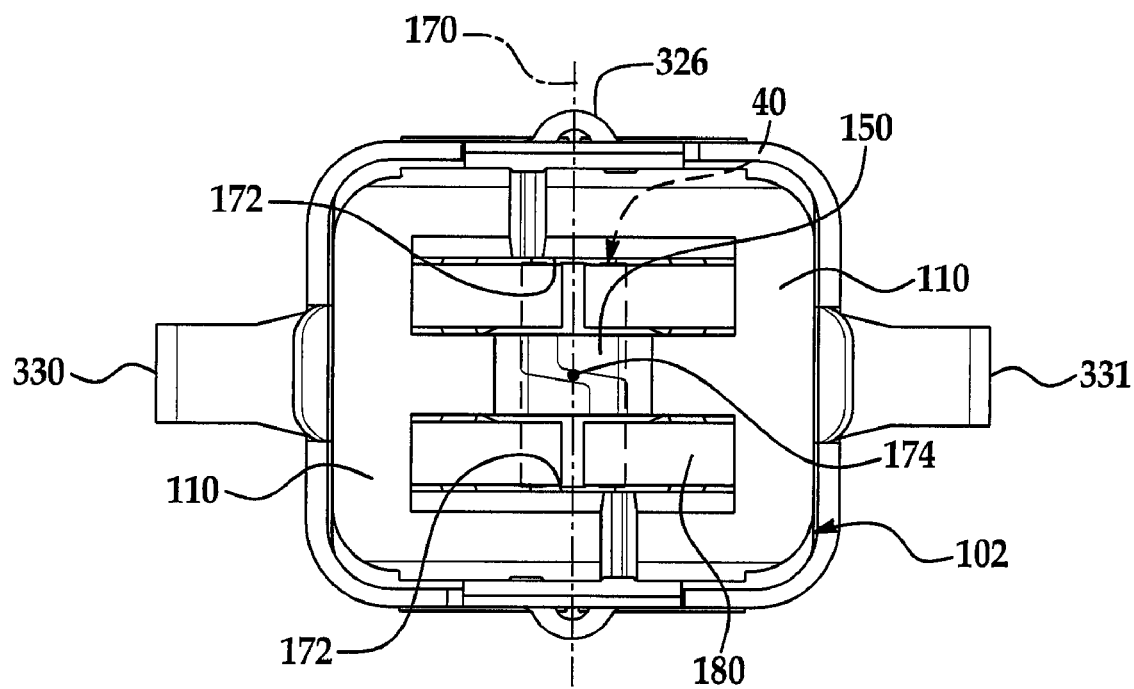
FIG. 24 is a perspective view of the electrical connector of FIG. 23 from the connection end in a hinged close position.

Ceramic connector body portions 110 may also be configured such that outermost terminal channels (in FIGS. 3-16 there are only two, so both are outermost) define a first end wall 134 and a second end wall 136, and an inner wall 138 is located between first end wall 134 and second end wall 136. Referring to FIGS. 3-10, 15 and 21-24, in an exemplary embodiment, the first end wall 134 and second end wall 136 may be configured such that first end wall 134 has an extension or extended portion 140 which extends above pivot portion 124 and second end wall 136 has a cavity 142 which is recessed from pivot portion 124, and wherein the respective extensions 142 and cavities 140 of the respective ceramic body portions 110 engage one another in mating or nested engagement. Extensions 142 extend above a mid-plane of the ceramic body 102 and sensor pocket 123 (i.e., a central cutting plane along the length of gas sensor 40 of FIG. 1 that passes between the opposed pivot portions) and cavities 140 are recessed below it. In this configuration, extensions 142 and cavities 140 prevent the mis-alignment of gas sensor 40 within the sensor pocket 123 because the respective extensions 142 on either side act as lateral or side stops preventing the sensor from inadvertently slipping out of the pocket during its insertion, as shown in FIGS. 21 and 24. The inner wall 138 may be configured to include an inwardly protruding member 144 which is offset from a centerline 148 of the inner wall, and wherein the respective inward protruding members 144 of the respective ceramic body portions 110 together provide a sensor stop surface 150 at the lower end of sensor pocket 123. As shown in FIGS. 3 and 5, ceramic connector body portions 110 may also be configured such that terminal channels also include a protrusion 146 opposite the retention pocket 126 which provides addition thickness of the body portion wall located thereunder, thereby strengthening the sidewall of ceramic body portions at that location.

Figure 17:
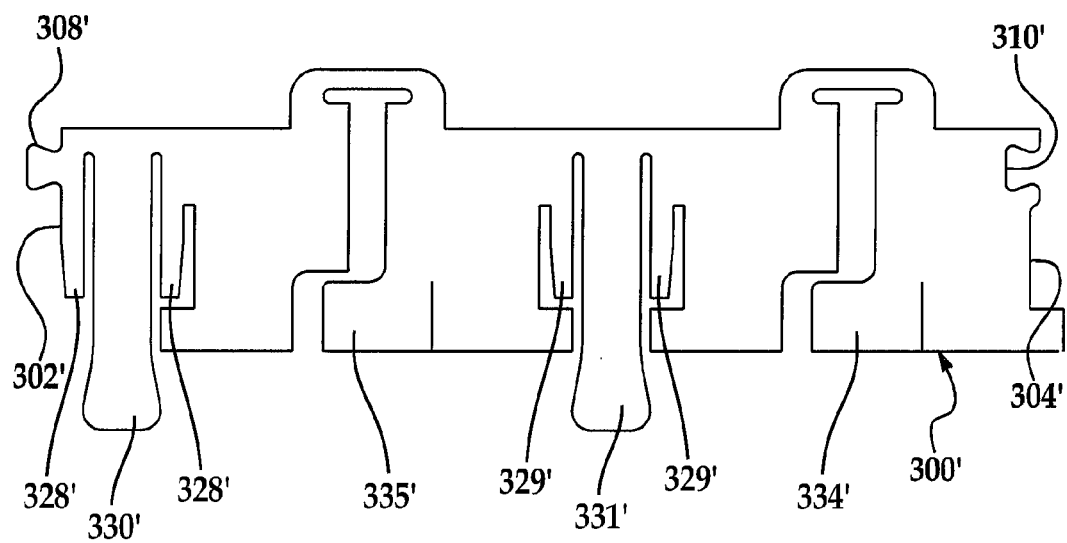
FIG. 17 is a top view of a precursor connector body retainer.
Figure 18:
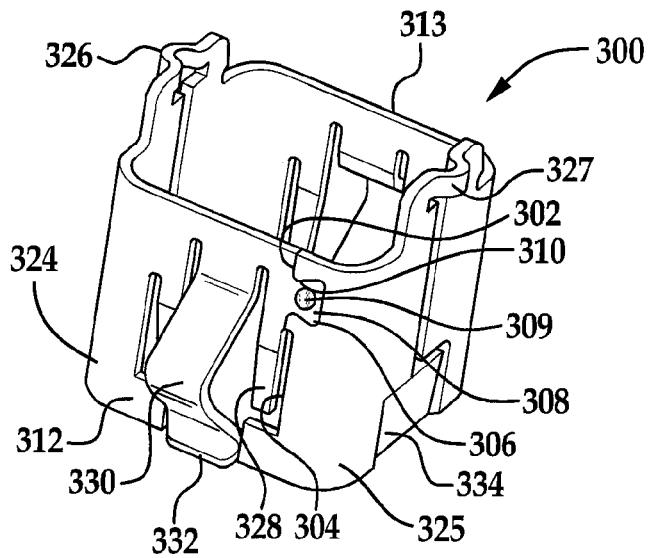
FIG. 18 is a top perspective view of a connector body retainer.
Figure 19:
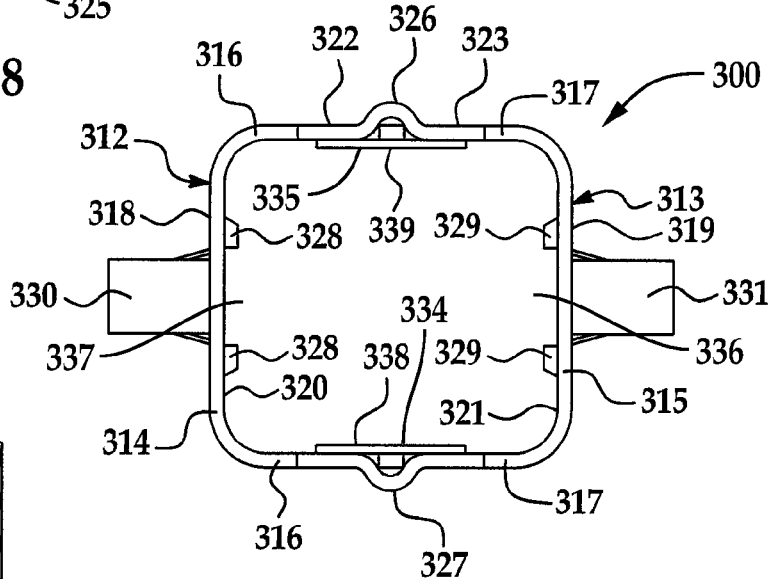
FIG. 19 is a top view of the connector body retainer of FIG. 18.

Referring to FIGS. 18 and 19, an exemplary embodiment of the present invention provides a connector body retainer 300. The connector body retainer 300 and the features thereof described herein may be formed from a precursor connector body retainer 300', as shown in FIG. 17. The precursor connector body retainer 300' may be formed by stamping the features shown from a metal sheet using a suitable die. Any suitable metal sheet may be used, but those having particularly good high temperature mechanical properties, such as tensile strength and creep resistance, oxidation resistance and corrosion resistance are particularly desirable. Suitable metals include various ferrous alloys, such as stainless steels, including high chrome stainless steel, high nickel stainless steel, as well as various Fe-base, Ni-base, and Cr-base superalloys. The various ferrous and other alloys described above are generally indicative of a wide number of metal alloys that are suitable for use as precursor connector body retainer 300'. In an exemplary embodiment, precursor connector body retainer 300' may be formed from a sheet of type 304 stainless steel (UNS 30400) having a thickness of about 0.2 mm. The precursor connector body retainer 300' may be formed using any suitable method, such as forming in a progressive die, into the connector body retainer 300 having the features described herein, as illustrated in FIGS. 18 and 19. The precursor connector body retainer 300' has a precursor first joint edge 302' and a precursor second joint edge 304' that are fixed to one another by a joint 306 during the process of forming connector body retainer 300 (FIG. 18). FIG. 18 shows the position of joint edge 302 in the formed connector body retainer 300, where joint edge 302 corresponds to precursor first joint edge 302' in the precursor connector body retainer of FIG. 17. FIG. 18 also shows the position of joint edge 304 in the formed connector body retainer 300, where joint edge 304 corresponds to precursor second joint edge 304' in the precursor connector body retainer of FIG. 17. The precursor first joint edge 302' has a protrusion 308' and the precursor second joint edge 304' has a recess 310' adapted for mating engagement with the protrusion 308'. The joint 306 may be any suitable joint and employ any suitable joining method, including various joints made by mechanical deformation, welding, brazing and the like. In an exemplary embodiment, joint 306 is a staked joint having a deformed portion 309 in one of the protrusion 308 or the recess 310 to fix the protrusion 308 in the recess 310. While the protrusion 308 and recess 310 shown in FIG. 18 interlock in of the manner of the locking tabs of a jigsaw puzzle, and then are fixed by staking, any suitable mating protrusion and recess configuration may be used.

The connector body retainer 300 includes a pair of retainer bands 312,313, each having a generally U-shaped or C-shaped profile with respective base portions 314,315 and respective pairs of opposed extending legs 316,317. The profile of the connector body retainer 300 is generally selected for mating engagement with the ceramic connector body 102; including the ceramic connector body portions 110 (see FIGS. 1 and 2). A generally U-shaped profile as shown in FIGS. 18 and 19 may be used with ceramic connector body portions that form a generally rectangular prism-shaped ceramic connector body 102 having a generally rectangular cross-sectional profile, while a generally C-shaped profile may be used with ceramic connector body portions 110 that form a generally cylindrical ceramic connector body 102 (not shown) having a generally circular cross-sectional profile.

The connector body retainer 300 includes a pair of retainer bands 312,313, each having a generally u-shaped or c-shaped profile with respective base portions 314,315 and respective pairs of opposed extending legs 316,317. The profile of the connector body retainer 300 is generally selected for mating engagement with the ceramic connector body 102; including the ceramic connector body portions 110 (see FIGS. 1 and 2). A generally u-shaped profile as shown in FIGS. 18 and 19 may be used with ceramic connector body portions that form a generally rectangular prism-shaped ceramic connector body 102 having a generally rectangular cross-sectional profile, while a generally c-shaped profile may be used with ceramic connector body portions 110 that form a generally cylindrical ceramic connector body 102 (not shown) having a generally circular cross-sectional profile.

The opposed outwardly extending legs 316,317 of each connector body retainer band 312,313 extend toward the other in opposing arrangement to provide the connector body retainer 300. Retainer bands 312,313 have respective an outer surfaces 318,319; inner surfaces 320,321; hinge ends 322,323 and insertion ends 324,325. The legs 316,317 of the respective retainer bands 312,313 which are in opposing arrangement are joined together by a respective pair of outwardly arched hinges 326,327 proximate the hinge end that join retainer bands 312,313. Outwardly arched hinges 326,327 are operative as spring members upon insertion of connector body portions 110,111 and permit the connector body retainer 300 to hinge open and closed in conjunction with the insertion of the gas sensor 40. The hinges, as spring members, may also be used to assist in the retention of connector body portions 110,111 if, upon insertion, they are sized together with the hinge ends 322,323 of the connector body retainer so as to create an interference between them upon insertion of the connector body portions 110,111 into connector body retainer 300. Hinges 326,327 may be designed and sized with respect to their length, width, radius of curvature, and thickness, together with the resultant mechanical properties of the material used upon deformation used to form the hinge, to obtain the desired characteristics as spring members. The retainer bands 312,313 may be formed as substantially identical, excepting the joint ends, bands in the opposing configuration described, or the bands may be different from one another and include the various elements described herein in different combinations or configurations.

Referring to FIGS. 1, 2, 17, 18 and 19, the retainer bands 312,313 may also include respective inwardly extending arms 328,329. In an exemplary embodiment, as shown in FIGS. 18 and 19, the respective retainer bands 312,313 each include two inwardly extending arms 328,329. The inwardly extending arms 328,329 are operative to capture the ceramic body portions 110,111. The inwardly extending arms 328,329 flex elastically outwardly during the insertion of the ceramic body portions 110,111, and then spring back inwardly into respective pockets formed in the ceramic body portions 110,111 to capture them in the respective retainer bands 312,313, and thus within connector body retainer 300. The inwardly extending arms 328,329 may be located in the base portion of the respective retainer bands 312,313 as shown in FIGS. 18 and 19; however, they may also be located in the respective legs 316,317 if the respective connector body portions 110,111 have a correspondingly located pocket, or in various combinations of the respective base portions and legs. The inwardly extending arms 328,329 are preferably formed as flat precursor inwardly extending arms 328',329' and plastically deformed during the process of transforming precursor connector body retainer 300' into connector body retainer 300; however, attachment of separate inwardly extending arms 328,329 is not precluded. The inwardly extending arms 328,329 may have the tapered inwardly extending profile shown in FIGS. 18 and 19 or other suitable inwardly extending profiles.

Referring to FIGS. 1, 2, 17, 18, 19, and 20A, the retainer bands 312,313 may also include respective outwardly extending arms 330,331. In an exemplary embodiment, as shown in FIGS. 18 and 19, the respective retainer bands 312,313 each include one outwardly extending arm 330,331; however, the bands may include more than one outwardly extending arm. The outwardly extending arms 330,331 are operative to capture the ceramic body portions 110,111. The outwardly extending arms 330,331 flex inwardly, either elastically, plastically or a combination thereof, during the crimping of precursor inner shield 80 to form inner shield 60 as shown in FIGS. 1 and 2. Outwardly extending arms 330,331 act as resilient spring members to apply a closing force respectively to ceramic body portions 110,111 and connector body retainer bands 312,313 and establish the desired contact force between the conductive terminals of the connector and contact pads of the gas sensor. In an exemplary embodiment, the outwardly extending arms 330,331 have an outwardly-bent bow shape and respective free ends 332,333. The free ends 332,333 are adapted for disposition in contact with the outer surfaces of the respective ceramic body portions 110,111 and may apply the closure for directly to them, as well as through the respective retainer bands 312,313. The outwardly extending arms 330,331 may be located in the base portion of the respective retainer bands 312,313 as shown in FIGS. 18 and 19; however, they may also be located in the respective legs 316,317, or in various combinations of the respective base portions and legs. The outwardly extending arms 330,331 are preferably formed as flat precursor outwardly extending arms 330',331' and plastically deformed during the process of transforming precursor connector body retainer 300' into connector body retainer 300; however, attachment of separate outwardly extending arms 330,331 is not precluded. The inwardly extending arms 328,329 may have the bow-shaped outwardly extending profile shown in FIGS. 18 and 19 or other suitable outwardly extending profiles.

Referring to FIGS. 1, 2, 17, 18 and 19, each of the retainer bands 312,313 may also include respective flex members 334,335 proximate the respective insertion ends 324,325 which protrude toward the other retainer band and a retainer cavity 336,337 which matingly receives the flex member of the other retainer band. In an exemplary embodiment, as shown in FIGS. 18 and 19, the respective retainer bands 312,313 each include respective flex members 334,335. The flex members 334,335 are operative to capture and provide alignment of the side walls of opposing ceramic body portions 111,110 upon hinged closure of the electrical connector 100. The retainer cavities 336,337 are sized to permit closure of electrical connector 100 and provide an opening sufficient to house flex members 334,335. The flex members 334,335 may be formed so as to extend or taper inwardly from the insertion end to further enhance the function described above by providing innermost edges 338,339 to capture the opposing connector body portions 111,110 rather than the inner surface of flex members 334,335. The flex members 334,335 are located in the respective legs 316,317 as shown in FIGS. 18 and 19. The flex members 334,335 are preferably formed as flat precursor flex members 334',335' and plastically deformed during the process of transforming precursor connector body retainer 300' into connector body retainer 300; however, attachment of separate flex members 334,335 is not precluded. The flex members 334,335 may have the tapered inwardly extending profile shown in FIGS. 18 and 19 or other suitable inwardly extending profiles.

Figure 22:
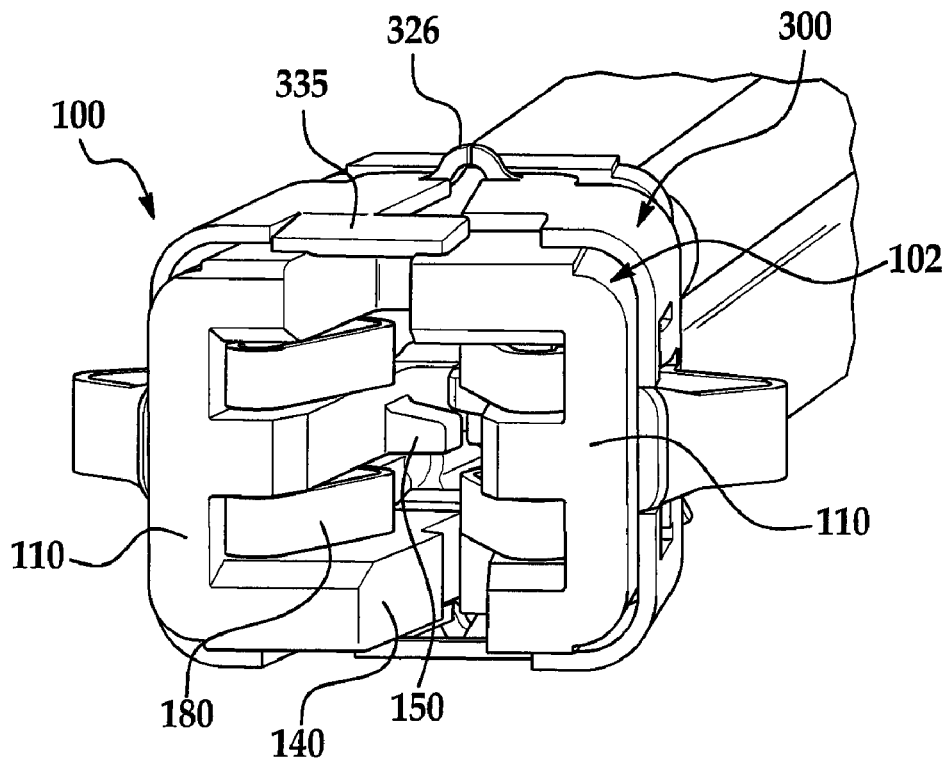
FIG. 22 is a perspective view of the electrical connector of FIG. 21 from the insertion end in a hinged open position.

An exemplary embodiment of an electrical connector 100 according to the present invention is shown in FIGS. 21-24. FIGS. 21 and 22 illustrate connector 100 in the hinged open position, such as would occur as sensor 40 is inserted into 100 connector in the manner described herein and illustrated, for example, by FIGS. 20A and 20B. As illustrated by the phantom representation of sensor 40 in FIG. 21, the overlap of sensor 40 and hinged open terminals 180 indicate that electrical contacts may be established upon insertion, since insertion of the actual sensor would cause deflection of terminals 180 corresponding to the amount of overlap shown. Thus, the magnitude of the insertion force may be controlled by controlling the overlap. The degree of overlap may be controlled by adjustment of the taper angle (θ) in the taper section 124. FIGS. 23 and 24 illustrate connector 100 in the hinged close position, such as would occur as sensor 40 is inserted into 100 connector in the manner described herein and illustrated, for example, by FIGS. 20C and 20D. As illustrated by the phantom representation of sensor 40 in FIG. 23, the larger amount of overlap of sensor 40 and hinged close terminals 180 indicates that electrical contacts have the full contact force upon completion of the crimping process and formation of upper shield 60. The degree of overlap may be controlled by the design of terminals 180, channels 130, outwardly extending arms 330,331 and other factors that influence the characteristics of the spring members that provide the spring bias and contact force applied to terminals 180. FIGS. 21-24 also illustrate how extensions 140 and recesses 142 cooperate to retain sensor 40 within sensor pocket 123 during insertion. Extensions 140 and recesses 142 cooperate to prevent sensor 40 from slipping out of sensor pocket 123 along the mid-plane 170 and guide the sensor 40 into sensor pocket 123 during insertion of sensor 40 into connector 100 by providing guide surfaces 172. The retainer 300 and body portion 102 may also be configured such that hinges are generally proximate the pivot portion, and may be located substantially co-axially with the pivot line 113.

Thus, another exemplary embodiment of the present invention may incorporate a method of assembly of a high temperature electrical connector 100, including a number of steps. One step of forming a pair of ceramic body portions 110, each ceramic body portion 110 having a terminal side 112 and a retainer side 114, a terminal end 118 and a connection end 116, and a pivot portion 120 on the terminal side proximate the sensor pocket 123, the ceramic body portions 110 disposed with the terminal sides 112 and connections ends 116 proximate one another and the pivot portions 120 in touching contact. The method also includes a second step of assembling at least two conductive terminals 180 within the sensor pocket portion (the pocket portions together forming sensor pocket 123) of each ceramic body portion 110, each terminal having a contact portion 182 located within the sensor pocket 123 and a termination portion 184 which extends from the ceramic body portion 110, each conductive terminal 180 being electrically isolated from every other non-associated conductive terminal 180. The method further includes a third step of forming a ceramic connector body 102 by disposing a pair of ceramic body portions 110 with the terminal sides 112 and connections ends 116 proximate one another and the pivot portions 120 in touching contact. The method further includes a fourth step of disposing the ceramic connector body 102 into a retainer 300 having a pair of retainer bands 312,313 each having a generally u-shaped or c-shaped profile with a base portion and a pair of opposed extending legs, the legs of each band 312,313 extending toward the other in opposing arrangement to provide the retainer, each retainer band 312,313 having an outer surface, an inner surface, a hinge end 322,323 and an insertion end, the legs of the respective bands which are in opposing arrangement are joined together by a respective pair of outwardly arched hinges 326,327 proximate the hinge end; the ceramic connector body disposed in the retainer with the retainer sides of respective ceramic body portions abutting the inner surfaces of the respective base portions with the arched hinges located proximate the terminal ends and terminal side of the ceramic body portions 110, wherein the ceramic body portions 110 are operative to open about the hinges 326,327 and pivot portions 120 to a clamshell configuration.

The step of disposing may also include inserting the ceramic connector body 102 into the retainer 300 along a longitudinal or z-axis 174 of the retainer in the direction shown by arrow 178. This is advantageous with regard to assembly of the connector 100, as compared with processes that require assembly of components, such as a retainer 300 from other directions. The base portion 314,315 of each retainer band 312,313 further may include an inwardly extending arm 328,329 and each of the ceramic body portions 110 further may include a retention pocket 126 in the retainer side and an outwardly protruding retainer flange 128 proximate the terminal end, wherein the step of disposing comprises inserting the connection ends 118 of the ceramic connector body 110 into the hinge ends 322,323 of the retainer until the hinge end 322,323 of the retainer 300 abuts the outwardly protruding retainer flanges 128 and the inwardly extending arms 328,329 engage the retention pockets 126, whereby the position of the retainer 300 is fixed relative to the ceramic connector body 110.

The method may provide that each of the terminals 180 is disposed in a terminal channel 130 in the respective ceramic body portion 110 which extends into the sensor pocket 123, each terminal channel has a terminal bore 132 which extends from the terminal channel 130 through the ceramic body portion 110 and provides an opening in the retainer side 114, and each terminal 180 has an attachment tang 186 on the termination portion 184 of the terminal 180, wherein the step of assembling the terminals 180 comprises inserting terminals 180 into the channels 130 with the contact portion 182 extending into the sensor pocket 123 and the attachment tang 186 through the terminal bore 132 so as to fix the terminal 180 to the ceramic body portion 110.

Thus, another exemplary embodiment of the present invention may include a method of making a high temperature gas sensor, including a number of steps. The method may include one step of forming a high temperature electrical connector comprising: a ceramic connector body comprising a pair of ceramic body portions, each ceramic body portion having on a side thereof a pivot portion and a sensor pocket portion, the ceramic body portions disposed with the pivot portions in touching contact and the pocket portions forming a sensor pocket; at least two conductive terminals located within the sensor pocket portion of each ceramic body portion, each terminal having a contact portion located within the sensor pocket portion and a termination portion which extends from the ceramic body portion; a retainer having a pair of retainer bands each having a generally U-shaped or C-shaped profile with a base portion and a pair of opposed extending legs, the legs of each band extending toward the other in opposing arrangement to provide the retainer, legs of the respective bands which are in opposing arrangement are joined together by a respective pair of outwardly arched hinges; the ceramic connector body disposed in the retainer, wherein the ceramic body portions are operative to hinge open about the hinges and pivot portions to a clamshell configuration. The method may include a second step of inserting a flat-plate ceramic sensor having a plurality of electrical contacts into the sensor pocket, whereby the ceramic body portions hinge open to receive the sensor. The method may include a third step of disposing an upper shield about the electrical connector and flat-plate ceramic sensor. The method may include a fourth step of biasing a spring member between the upper shield and the electrical connector so as to apply a predetermined normal contact force between each conductive terminal and the respective electrical contact sufficient to establish power or signal communication between them.

The method may also include a step of forming a sensor subassembly incorporating the flat-plate ceramic sensor prior to the step of inserting the sensor into the electrical connector, the sensor assembly comprising a sensor shell having an attachment portion, a sealing portion and a central bore; a packing disposed in sealing and compressed engagement within the central bore; and the flat-plate ceramic sensor having a reference end and a sensing end, which is sealingly disposed within the packing in the central bore, the reference end extends from the sealing portion and the sensing end extends from the attachment portion, the reference end having the plurality of electrical contacts.

The method may provide that each of the retainer bands includes an outwardly extending arm, wherein the step of biasing comprises crimping the upper shield to compress the outwardly extending arm.

The method may also provide that the predetermined contact force produced by crimping is at least 2 $lb_f$.

The method may also provide that each of the retainer bands comprises an outwardly extending arm, wherein the step of biasing includes crimping the upper shield to compress the outwardly extending arm. The method may also provide that the upper shield further includes a seal end and a shell end, the gas sensor further includes a seal proximate the electrical connector disposed in the seal end of the upper shield, the sealing portion of the shell is disposed in the shell end of the upper shield, and crimping further includes deforming the upper shield to form a first sealed joint between the seal and the upper shield and a second sealed joint between the shell and the upper shield.

The method may also include a step of attaching a lower shield to the attachment portion of the shell.

The method may also provide that each of the terminals is disposed in a terminal channel in the respective ceramic body portion which extends into the sensor pocket and each of the conductive terminals has an inwardly-bent bow portion and the contact portion is proximate an apex of the inwardly-bent bow. The method may also provide that each of the outwardly extending arms has an outwardly extending bow portion and the upper shield is compressed against an apex of each outwardly extending bow. The method may also provide that lines of normal force between the terminals and the electrical contacts and lines of normal force between the outwardly extending arms upper shield are substantially co-planar.

The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

What is claimed is:

1. A high temperature gas sensor (10), comprising:
a sensor shell (30) having an attachment portion (35), a sealing portion (36) and a central bore (34);
a packing disposed in sealing and compressed engagement within the central bore (34);
a flat-plate ceramic sensor (40) having a reference end and a sensing end (12), which is sealingly disposed within the packing in the central bore (34), the reference end extends from the sealing portion (36) and the sensing end extends from the attachment portion (35), the reference end having a plurality of electrical contacts;
an electrical connector assembly (100) comprising a ceramic connector body (110) having a pair of ceramic body portions (111), each having a pivot portion (120) and a plurality of conductive terminals disposed in a sensor pocket portion (122), the pivot portions (120) and sensor pocket portions (122) disposed in opposing relation to form a sensor pocket (123), and a retainer having a pair of retainer bands (312, 313), each having a generally U-shaped or C-shaped profile comprising a base portion and a pair of opposed extending legs (316, 317), the legs of each band extending toward the other in opposing arrangement to provide the retainer (114), the legs of the respective bands which are in opposing arrangement are joined together by a respective pair of outwardly arched hinges (326, 327) opposite the sensor pocket (122), the conductive terminals, in signal or power communication with the electrical contacts of the sensor and the ceramic connector body (102) disposed in the retainer (114); wherein the ceramic body portions (110, 111) are operative to pivot about the pivot portions (120) in a hinged clamshell configuration and provide a contact force between the conductive terminal and the respective electrical contact;

a sealing member (58) proximate the electrical connector assembly (100) disposed opposite the flat-plate sensor (40);

an upper shield (60) having an upper shield bore (60), a shell end and a seal end, the shell end sealingly engaged with the sealing portion (36) of the sensor shell (30), the seal end sealingly engaged with the sealing member (58) and the electrical connector assembly (100) disposed within the upper shield bore (60); and a spring member disposed within the upper shield bore (60) and biased between the upper shield member and the retainer (114).

2. The gas sensor (10) of claim 1, further comprising a lower shield attached to the attachment portion (35) of the shell (30) and disposed about the sensing end (42) of the sensor (10).

3. The gas sensor (10) of claim 1, wherein the base portion of each retainer band (312, 313) further comprises an inwardly extending arm (328, 329).

4. The gas sensor (10) of claim 3, wherein each of the ceramic body portions (110, 111) further comprises a retention pocket (126) proximate the retainer (114) and an outwardly protruding retainer flange (128), the retainer (114) abuts the outwardly protruding retainer flange (128) and the inwardly extending arm (328, 329) engages the retention pocket (126), and whereby the position of the retainer is fixed relative to the ceramic connector body (110, 111).

5. The gas sensor (10) of claim 4, wherein each retention pocket (126) tapers inwardly.

6. The gas sensor (10) of claim 4, wherein the inwardly extending arm (328, 329) comprises at least two inwardly extending arms (328, 329) on each retainer band (312, 313).

7. The gas sensor (10) of claim 4, wherein each retainer band (312, 313) further comprises an outwardly extending arm (330, 331).

8. The gas sensor (10) of claim 1, wherein the base portion of each retainer band (312, 313) further comprises an outwardly extending arm (330, 331), and the outwardly extending arms (330, 331) comprise the spring member.

9. The gas sensor (10) of claim 8, wherein each of the outwardly extending arms (330, 331) has an outwardly-bent bow shape and a free end (332, 333).

10. The gas sensor (10) of claim 9, wherein the free end (332, 333) engages the retainer surface.

11. The gas sensor (10) of claim 1, wherein each retainer band (312, 313) further comprises a flex member (334, 335) spaced from the hinges which protrudes toward the other retainer band (312, 313) and a retainer cavity (336, 337) which matingly receives the flex member (334, 335) of the other retainer band (312, 313).

12. The gas sensor (10) of claim 11, wherein the flex member (334, 335) tapers inwardly from the insertion end (324, 325).

13. The gas sensor (10) of claim 1, wherein each of the terminals is disposed in a terminal channel (130) in the respective ceramic body portion (110, 111) which extends into the sensor pocket (123), outermost terminal channels (130) define a first end wall (134) and a second end wall (136), and an inner wall (138) is located between the first end wall (134) and a second end wall (136).

14. The gas sensor (10) of claim 13, wherein the first end wall (134) has an extension which extends above the pivot portion (120) and the second end wall (136) has a cavity (140) which is recessed from the pivot portion (120), and wherein the respective extensions (142) and cavities (140) of the respective ceramic body portions (110, 111) engage one another.

15. The gas sensor (10) of claim 14, wherein the inner wall (138) has an inward protruding member which is offset from a centerline (113) of the inner wall (138), and wherein the respective inward protruding members of the respective ceramic body portions (110, 111) provide a sensor stop (150), and the reference end of the flat-plate ceramic sensor (40) is proximate the sensor stop (150).

16. The gas sensor (10) of claim 13, wherein the inner wall (138) has an inward protruding member which is offset from a centerline (113) of the inner wall (138), and wherein the respective inward protruding members of the respective ceramic body portions (110, 111) provide a sensor stop (150), and the reference end of the flat-plate ceramic sensor (40) is proximate the sensor stop (150).

17. The gas sensor (10) of claim 1, wherein the ceramic body portions (110, 111) are identical.

18. A method of making a high temperature gas sensor (10), comprising the steps of:

forming a high temperature electrical connector assembly (100) comprising: a ceramic connector body (102) comprising a pair of ceramic body portions (110, 111), each ceramic body portion (110, 111) having on a side thereof a pivot portion (120) and a sensor pocket portion (122), the ceramic body portions (110, 111) disposed with the pivot portions (120) in touching contact and the pocket portions forming a sensor pocket (123); at least two conductive terminals located within the sensor pocket portion (122) of each ceramic body portion (110, 111), each terminal having a contact portion located within the sensor pocket portion (122) and a termination portion which extends from the ceramic body portion (110, 111); a retainer (114) having a pair of retainer bands (312, 313) each having a generally U-shaped or C-shaped profile with a base portion (314, 315) and a pair of opposed extending legs (316, 317), the legs of each band extending toward the other in opposing arrangement to provide the retainer (114), legs of the respective bands (312, 313) which are in opposing arrangement are joined together by a respective pair of outwardly arched hinges (326, 327); the ceramic connector body (102) disposed in the retainer (114), wherein the ceramic body portions (110, 111) are operative to hinge open about the hinges and pivot portions (120) to a clamshell configuration;

inserting a flat-plate ceramic sensor (40) having a plurality of electrical contacts into the sensor pocket (123), whereby the ceramic body portions (110, 111) hinge open to receive the sensor (10);

disposing an upper shield (60) about the electrical connector assembly (100) and flat-plate ceramic sensor (40); and biasing a spring member between the upper shield (60) and the electrical connector assembly (100) so as to apply a predetermined normal contact force between each conductive terminal and the respective electrical contact sufficient to establish power or signal communication between them.

19. The method of claim 18, further comprising a step of forming a sensor assembly incorporating the flat-plate ceramic sensor (40) prior to the step of inserting the sensor (40) into the electrical connector assembly, the sensor assembly comprising a sensor shell (30) having an attachment portion (35), a sealing portion (36) and a central bore (34); a packing disposed in sealing and compressed engagement within the central bore (34); and the flat-plate ceramic sensor (40) having a reference end and a sensing end (12), which is sealingly disposed within the packing in the central bore (34), the reference end extends from the sealing portion (36) and the sensing end (12) extends from the attachment portion (35), the reference end having the plurality of electrical contacts.

20. The method of claim 19, wherein each of the retainer bands (312, 313) comprises an outwardly extending arm (330, 331), and wherein the step of biasing comprises crimping the upper shield (60) to compress the outwardly extending arm (330, 331).

21. The method of claim 20, wherein the upper shield (60) further comprises a seal end and a shell end, the gas sensor (10) further comprises a seal proximate the electrical connector assembly disposed in the seal end of the upper shield (60), the sealing portion (36) of the shell (30) is disposed in the shell end of the upper shield (60), and crimping further comprises deforming the upper shield (60) to form a first sealed joint between the seal and the upper shield (60) and a second sealed joint between the shell and the upper shield (60).

22. The method of claim 21, further comprising a step of attaching a lower shield (20) to the attachment portion (35) of the shell (30).

23. The method of claim 18, wherein each of the retainer bands (312, 313) comprises an outwardly extending arm (330, 331), and wherein the step of biasing comprises crimping the upper shield (60) to compress the outwardly extending arm (330, 331).

24. The method of claim 23, wherein the predetermined contact force produced by crimping is at least 2 $lb_f$.

25. The method of claim 23, wherein each of the terminals is disposed in a terminal channel (130) in the respective ceramic body portion (110, 111) which extends into the sensor pocket (123) and each of the conductive terminals has an inwardly-bent bow portion and the contact portion (182) is proximate an apex of the inwardly-bent bow.

26. The method of claim 25, wherein each of the outwardly extending arms (330, 331) has an outwardly extending bow portion and the upper shield (60) is compressed against an apex of each outwardly extending bow.

27. The method of claim 26, wherein lines of normal force between the terminals and the electrical contacts and lines (113) of normal force between the outwardly extending arms (330, 331) upper shield (60) are substantially co-planar.

* * * * *